(12) United States Patent
Espina et al.

(10) Patent No.: US 10,842,895 B1
(45) Date of Patent: *Nov. 24, 2020

(54) GERMICIDAL MODULAR MOTION-DETECTING LIGHTING SYSTEM FOR SWITCHING BETWEEN VISIBLE LIGHT ILLUMINATION AND OPTICAL DISINFECTION

(71) Applicant: Great Home Tek Inc., San Jose, CA (US)

(72) Inventors: Jose M. Espina, Gilroy, CA (US); Alan Ghahramani, San Jose, CA (US); David Cook, Morgan Hill, CA (US)

(73) Assignee: Great Home Tek, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/883,877

(22) Filed: May 26, 2020

Related U.S. Application Data

(63) Continuation-in-part of application No. 16/680,307, filed on Nov. 11, 2019, now Pat. No. 10,813,201.

(51) Int. Cl.
    *F21V 21/005* (2006.01)
    *A61L 2/10* (2006.01)
    (Continued)

(52) U.S. Cl.
    CPC ............... *A61L 2/10* (2013.01); *A61L 2/24* (2013.01); *F21S 2/005* (2013.01); *F21V 21/005* (2013.01);
    (Continued)

(58) Field of Classification Search
    CPC .. F21V 21/002; F21V 21/005; F21V 23/0442; F21V 23/0471; F21V 23/06;
    (Continued)

(56) References Cited

U.S. PATENT DOCUMENTS 4,223,598 A * 9/1980 Suzuki ...................... B03C 3/32
                                                                422/121
4,786,812 A * 11/1988 Humphreys .............. A61L 9/20
                                                                250/455.11
(Continued)

OTHER PUBLICATIONS

Li, J., et al., "Enhanced Germicidal Effects of Pulsed UV-LED Irradiation on Biofilms," Journal of Applied Microbiology, ISSN 1364-5072, 109, pp. 2183-2190, 2010.

*Primary Examiner* — Ismael Negron
(74) *Attorney, Agent, or Firm* — Patent Ingenuity, P.C.; Samuel K. Simpson

(57) ABSTRACT

A germicidal motion-detecting lighting system includes a plurality of lighting units configured to electrically connect to one another. Each modular lighting unit has an enclosure, having an enclosure, a light emission window positioned within a first cavity of the enclosure, and a plurality of light emitting diodes positioned within the first enclosure, at least one motion sensor that protrudes through a second cavity of the enclosure, and a processor positioned within the enclosure that detects motion of a user based on data received from the at least one motion sensor and generates an activation command to emit visible light based on the motion of the user. The plurality of light emitting diodes receives the command and emits visible light based on the command. One of the modular lighting units further includes an additional enclosure with a third cavity in which an additional light emission window is positioned to emit ultraviolet light via an additional plurality of light emitting diodes.

20 Claims, 16 Drawing Sheets

(51) Int. Cl.
*F21S 2/00* (2016.01)
*F21V 23/04* (2006.01)
*A61L 2/24* (2006.01)
*F21V 23/06* (2006.01)
*F21Y 115/10* (2016.01)
*F21Y 113/17* (2016.01)

(52) U.S. Cl.
CPC .......... *F21V 23/0471* (2013.01); *F21V 23/06* (2013.01); *A61L 2202/11* (2013.01); *A61L 2202/14* (2013.01); *F21Y 2113/17* (2016.08); *F21Y 2115/10* (2016.08)

(58) Field of Classification Search
CPC ...... A61L 2/10; A61L 9/20; F21S 4/20; F21S 4/28

See application file for complete search history.

(56) References Cited

U.S. PATENT DOCUMENTS

| | | | | |
|---|---|---|---|---|
| 6,536,924 B2* | 3/2003 | Segretto | .................... | F21S 4/28 |
| | | | | 362/345 |
| 7,922,354 B2* | 4/2011 | Everhart | ............... | F21V 23/009 |
| | | | | 362/235 |
| 8,466,433 B2* | 6/2013 | Ullman | .................... | A61L 2/10 |
| | | | | 250/455.11 |
| 8,581,522 B2* | 11/2013 | Inskeep | .................... | A61L 2/10 |
| | | | | 315/360 |
| 8,939,634 B2* | 1/2015 | Leadford | ................ | F21S 2/005 |
| | | | | 362/647 |
| 9,759,391 B1* | 9/2017 | Shew | .................... | F21V 23/023 |
| 9,855,353 B1* | 1/2018 | Stacy | ........................ | A61L 2/24 |
| 9,964,289 B2* | 5/2018 | Pearson | ................ | F21V 21/005 |
| 2007/0053188 A1* | 3/2007 | New | ........................ | B64D 13/00 |
| | | | | 362/276 |
| 2010/0271804 A1* | 10/2010 | Levine | .................... | F21S 4/20 |
| | | | | 362/35 |
| 2016/0003456 A1* | 1/2016 | Xu | ........................ | F21V 23/003 |
| | | | | 362/249.06 |

\* cited by examiner

GERMICIDAL MODULAR MOTION-DETECTING LIGHTING SYSTEM FOR SWITCHING BETWEEN VISIBLE LIGHT ILLUMINATION AND OPTICAL DISINFECTION

RELATED APPLICATIONS

This patent application is a Continuation-In-Part application of U.S. patent application Ser. No. 16/680,307, filed on Nov. 11, 2019, entitled MODULAR MOTION-DETECTED LIGHTING SYSTEM, which is hereby incorporated by reference in its entirety.

BACKGROUND

1. Field

This disclosure generally relates to lighting systems. More particularly, the disclosure relates to motion-detected lighting systems.

2. General Background

Lighting systems are often necessary to help ensure the safety of the occupants of a home. For example, at night, lighting systems allow occupants to move about the home from room to room with minimal concern regarding stumbling over, or colliding with, objects.

However, installation of a lighting system is often a daunting task. In particular, lighting systems often come in predefined lengths that may or may not fit within a desired area for installation (e.g., underneath a kitchen cabinet). Further, even if the lighting system does fit within the desired area, it may not span the entirety of the intended area to be lit. In essence, home occupants are left with attempting to retrofit lighting systems of predefined measurements into preexisting homes that may not be capable of accommodating an optimal, or possibly any, fit.

As a result, many current home lighting configurations have inadequate lighting to ensure the safety of the home's occupants.

Furthermore, with an alarming rate of frequency, the safety of the home's occupants has been facing additional challenges in the form of viruses, fungi, and bacteria, such as antibiotic-resistant bacteria, present on various surfaces (e.g., kitchen countertops) within the home. As examples, viruses such as influenza and corona virus disease nineteen ("COVID-19") have threatened the lives of many people on a global scale. Such infirmities have been linked to contact with respiratory droplets, emanating from humans (e.g., sneezing, coughing, etc.), which may be present on surfaces. Additionally, albeit to a lesser degree, pathogens such as *E. coli* and *salmonella* have also presented food safety hazards that have threatened the lives of many.

Yet, even though sanitary conditions in living spaces has to be a high priority for the safety and well-being of the inhabitants of a home, current approaches are typically unsafe for the inhabitants, especially children. For example, many chemical disinfectants comprise harsh toxins that may have detrimental effects to the health of humans. Additionally, ozone treatments for disinfection run the risk of potential respiratory damage.

Accordingly, current sanitization approaches may be effective in performing disinfection within a home, but may encompass potentially harmful effects to human health. Additionally, such approaches may emit onerous odors that are not appealing to inhabitants or guests.

SUMMARY

In one embodiment, a motion-detected lighting system has a primary modular lighting unit having a first enclosure. Furthermore, the primary modular lighting unit has a first light emission window that is positioned within a first cavity of the first enclosure. Additionally, the primary modular lighting unit has a first plurality of light emitting diodes ("LEDs") that are positioned within the first enclosure. Also, the primary modular lighting unit has at least one motion sensor that protrudes through a second cavity of the first enclosure. Finally, the primary modular lighting unit has a processor positioned within the first enclosure that detects motion of a user based on data received from the at least one motion sensor and generates a command to emit light based on the motion of the user. The first plurality of LEDs receives the command and emits a first light emission based on the command.

The motion-detected lighting system also has an extender modular lighting unit, which has a second enclosure. Furthermore, the extender modular lighting unit has a second light emission window that is positioned within a first cavity of the second enclosure. Additionally, the extender modular lighting unit has a second plurality of LEDs that are positioned within the second enclosure. The second plurality of LEDs receives the command and emits a second light emission, simultaneously with the first light emission, based on the command.

In another embodiment, a motion-detected lighting system has the foregoing primary modular lighting unit and the foregoing extender modular lighting unit. Additionally, the motion-detected lighting system has one more receptacles that adhere to an object in a physical environment. The primary modular lighting unit has one or more first connectors that adhere at least a portion of the first enclosure to one or more undersides of the one or more receptacles. Further, the extender modular lighting unit has one or more second connectors that adhere at least a portion of the second enclosure to the one or more undersides of the one or more receptacles.

In yet another embodiment, a germicidal motion-detected lighting system has a primary modular lighting unit having a first enclosure, a first light emission window that is positioned within a first cavity of the first enclosure, a first plurality of LEDs that are positioned within the first enclosure, at least one motion sensor that protrudes through a second cavity of the first enclosure, and a processor positioned within the first enclosure that detects motion of a user based on data received from the at least one motion sensor and generates an activation command to emit visible light based on the motion of the user. The first plurality of LEDs receives the command and emits visible light based on the command. Furthermore, the germicidal motion-detected lighting system has an extender modular lighting unit having a second enclosure, a second light emission window that is positioned within a first cavity of the second enclosure, and a second plurality of LEDs that are positioned within the second enclosure. The second plurality of LEDs emits ultraviolet light prior to the processor detecting the motion of the user. Also, the second plurality of LEDs ceases to emit the ultraviolet light upon the processor detecting the motion of the user based on a deactivation command received from the processor.

In another embodiment, a germicidal motion-detected lighting system has a primary modular lighting unit having a first enclosure, a first light emission window that is positioned within a first cavity of the first enclosure, a first plurality of LEDs that are positioned within the first enclosure, at least one motion sensor that protrudes through a second cavity of the first enclosure, and a processor positioned within the first enclosure that detects motion of a user based on data received from the at least one motion sensor and generates an activation command to emit ultraviolet light based on motion inactivity of the user. The first plurality of LEDs receives the command and emits the ultraviolet light based on the command. Additionally, the germicidal motion-detected lighting system has an extender modular lighting unit having a second enclosure, a second light emission window that is positioned within a first cavity of the second enclosure, and a second plurality of LEDs that are positioned within the second enclosure. The second plurality of LEDs emits visible light subsequent to the processor detecting the motion of the user. Also, the second plurality of LEDs ceases to emit the ultraviolet light upon the processor detecting the motion of the user based on a deactivation command received from the processor.

BRIEF DESCRIPTION OF THE DRAWINGS

The above-mentioned features of the present disclosure will become more apparent with reference to the following description taken in conjunction with the accompanying drawings wherein like reference numerals denote like elements and in which.

DETAILED DESCRIPTION

A modular motion-detected lighting system is provided to allow for multiple lighting units to be adhered to one another in a configuration that meets the sizing requirements of a particular object within a physical environment. In essence, a user may select as many units as desired for attachment along a linear path for adherence to an object (kitchen cabinet, staircase railing, shelves, mirrors, etc.). As an example, the modular motion-detected lighting units may be adhered to one another via one or more magnetic connectors, allowing for easy installation and removal. Rather than being tied to a particular lighting installation, the modular motion-detected lighting system allows users to seamlessly move modular units from room-to-room and essentially snap units in place (e.g., via magnetic connection). Furthermore, the modular motion-detected lighting system may have one or more receptacles that adhere the modular motion-detected lighting units to the object. The receptacle(s) may be adhered (e.g., adhesive such as double-sided tape or glue, magnets, clips, etc.) to the intended location via tool-less installation (i.e., without a hammer or screwdriver). (Alternatively, screws, bolts, pins, nails, etc. may be used to adhere the receptacle(s) to the intended location.) For example, the modular motion-detected lighting system is easy-to-install on the underside of a number of different objects (e.g., kitchen cabinets, staircase rail, shelves, mirrors, etc.).

To maximize efficiency, the modular motion-detected lighting system may have a primary modular lighting unit and one or more extender modular lighting units. The primary modular lighting unit may be responsible for having certain componentry that performs operations for the modular motion-detected lighting system, whereas the one or more extender modular lighting units may have less componentry, and rely on the primary modular lighting unit for performing certain functionality for the overall modular-detected lighting system.

Additionally, in one embodiment, the modular motion-detected lighting system may utilize light emitters (e.g., LEDs) that emit light less brightly than standard light bulbs. In contrast with the use of standard light bulbs at night, whereby many users' eyes have to adjust to significant light intensity, the modular motion-detected lighting system may utilize LEDs, which emit light in a more comforting way to the eyes of the user. In essence, the modular motion-detected lighting system removes the physical coupling between a light bulb and a switch, which is present in many typical configurations.

Figure 1A:
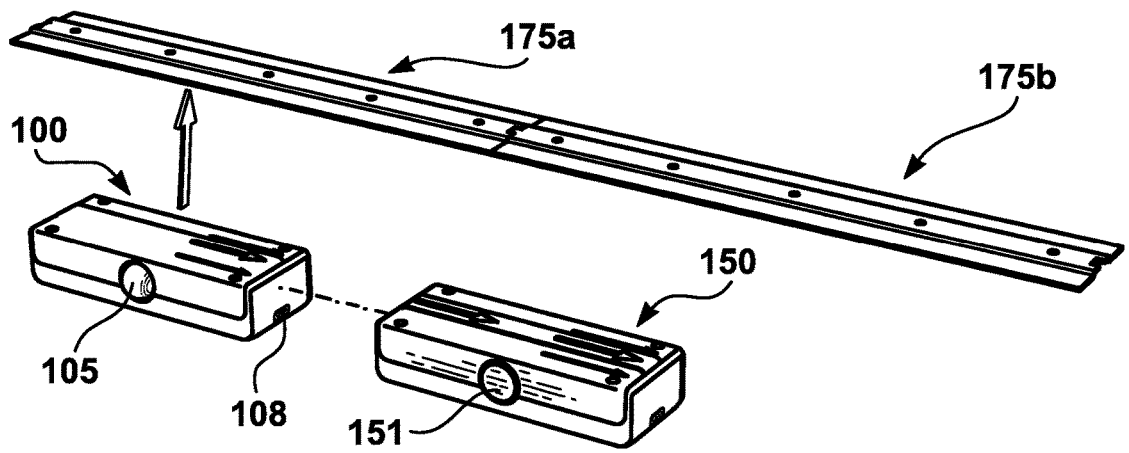
FIG. 1A illustrates a front, side perspective view of a primary modular lighting unit and an extender modular lighting unit, detached from each other and detached from a plurality of receptacles.

FIGS. 1A-1D illustrate side perspective views of a modular motion-detected lighting system 100. In particular, FIG. 1A illustrates a front, side perspective view of a primary modular lighting unit 100 and an extender modular lighting unit 150, detached from each other and detached from a plurality of receptacles 175a and 175b. The primary modular lighting unit 100 may have a connector 108, as illustrated by a side perspective view in FIG. 1C, positioned within the primary modular lighting unit 100 that connects to a receiver 109, as illustrated by a side perspective view in FIG. 1D, positioned within the extender modular lighting unit 151. In one embodiment, the connector 108 and the receiver 109 encompass one or more magnets that adhere the primary modular lighting unit 100 and the extender modular lighting unit 150 to one another. (Alternatively, the primary modular lighting unit 100 may have the receiver 109, and the extender modular lighting unit 150 may have the connector 108.) In another embodiment, a different type of connection mechanism (e.g., one or more clips), may be utilized to adhere the primary modular lighting unit 100 and the extender modular lighting unit 151 to one another.

The connector 108 and the receiver 109 may be electronically coupled, when adhered to one another, to allow for the transmission of electrical charge from the primary modular lighting unit 100 to the extender modular lighting unit 150. Accordingly, in one embodiment, the primary modular lighting unit 100 may be responsible for generating electricity (e.g., via an internal battery, connection to an external A/C adapter, etc.), thereby alleviating the extender modular lighting unit 150 of the responsibility for generating electricity.

Furthermore, in one embodiment, the primary modular lighting unit 100 may be responsible for performing motion detection for the modular motion-detected lighting system, thereby alleviating the extender modular lighting unit 150 of that responsibility. For example, the primary modular lighting unit 100 may have a motion sensor 105, which includes a geometrically-shaped casing that surrounds a motion sensing element (e.g., an infrared ("IR") sensor that is able to detect movement in the dark). For example, the casing may be a spherical, or semi-spherical (i.e., substantially spherical), shape. By having such a shape, the casing allows for a field of view that provides significant detection of movement. For instance, the motion sensor 105 may detect motion within a field of view of approximately one hundred eighty degrees from the motion sensor 105. (Other fields of view, which are lesser or greater than this example, may be obtained based on different geometrical shapes of the casing.) By way of contrast, the extender modular lighting unit 150 may be configured to not have any motion sensor. For example, the extender modular lighting unit 150 may have a non-motion sensing element 151 that is positioned within a cavity that could be filled with the motion sensor. In other words, both the primary modular lighting unit 100 and the extender modular lighting unit 150 may be fabricated from the same shell, but the motion sensor 105 may be implemented for the primary modular lighting unit 100, whereas the non-motion sensing element 151 may be implemented for the extender modular lighting unit 150. In another embodiment, different shells may be utilized for the primary modular lighting unit 100 and the extender modular lighting unit 150. For example, the extender modular lighting unit 150 may have a continuous outer wall, without any cavity for a non-motion sensing element 151.

In one embodiment, the receptacles 175a and 175b are also modular. For example, two modular lighting units may fit on the receptacle 175a, thereby necessitating an additional receptacle 175b for additional modular lighting units. In another embodiment, the receptacle 175a is not modular.

Figure 1B:
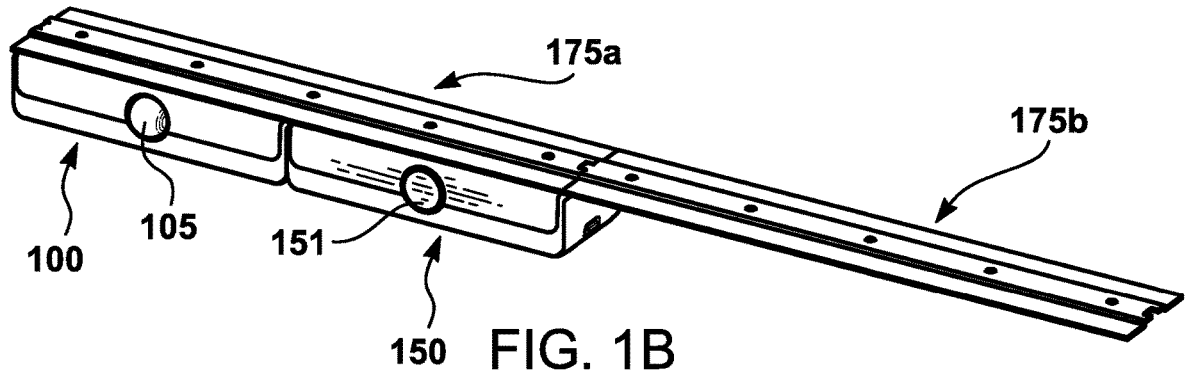
FIG. 1B illustrates the primary modular lighting unit and the extender modular lighting unit being adhered to one another, and being adhered to the receptacle.
Figures 1C, 1D:
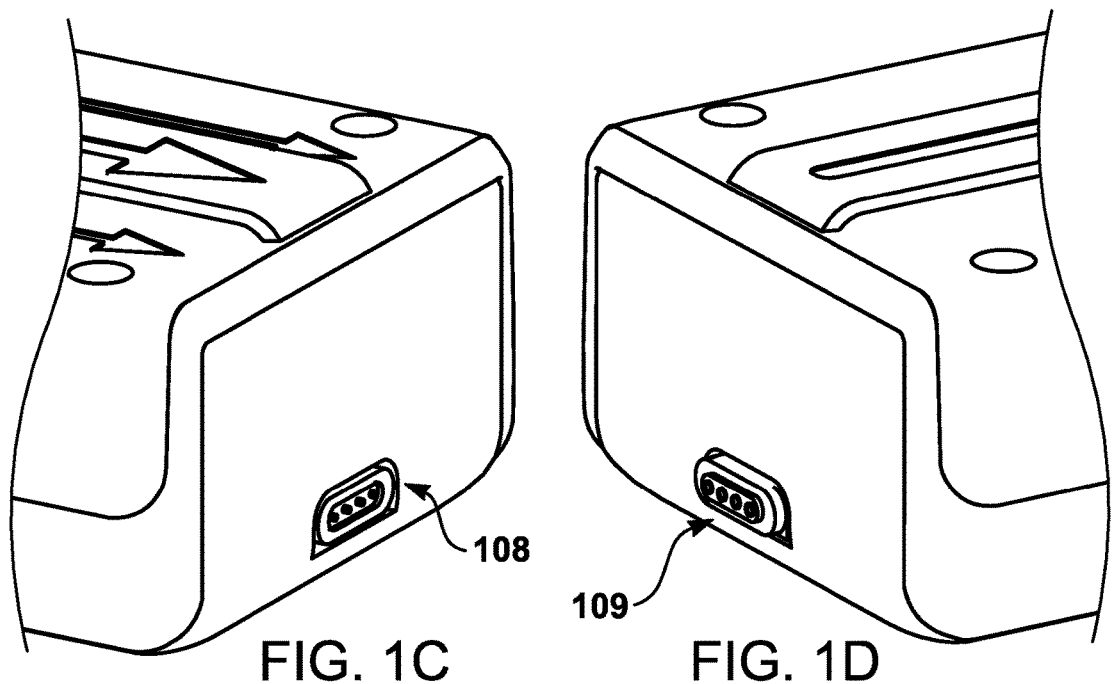
FIG. 1C illustrates a side perspective view of a connector positioned within the primary modular lighting unit.
FIG. 1D illustrates a side perspective view of a receiver positioned within the extender modular lighting unit.

Furthermore, FIG. 1B illustrates the primary modular lighting unit 100 and the extender modular lighting unit 150 being adhered to one another, and being adhered to the receptacle 175a. In one embodiment, each of the primary modular lighting unit 100 and the extender modular lighting unit 150 have a plurality of magnets that allow the primary modular lighting unit 100 and the extender modular lighting unit 150 to be adhered to one or more of the receptacles 175a and 175b.

Figure 2A:
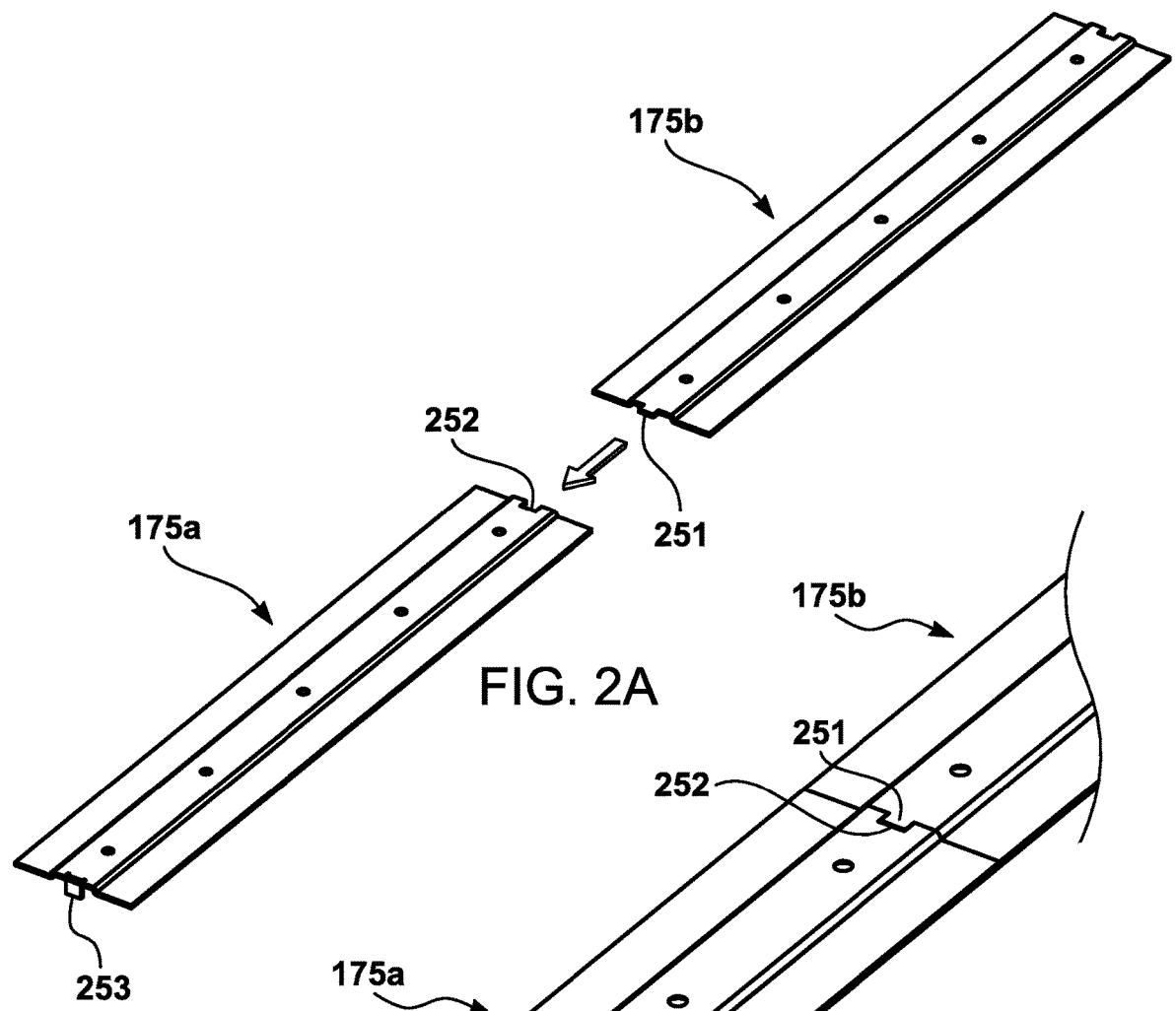
FIG. 2A illustrates a top perspective view of the receptacles detached from one another.
Figure 2B:
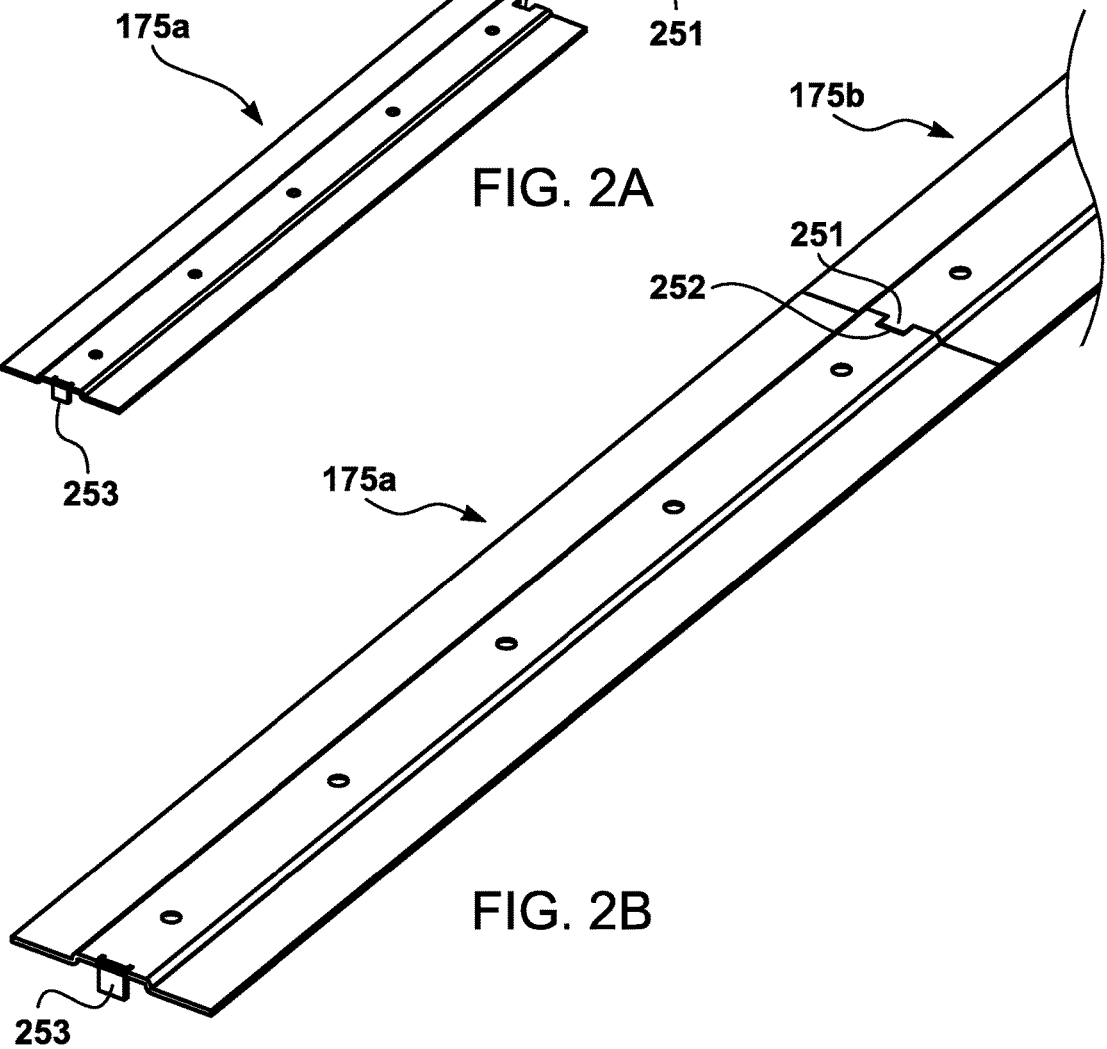
FIG. 2B illustrates the receptacles adhered to one another.

FIGS. 2A and 2B illustrate top perspective views of the receptacles 175a and 175c illustrated in FIGS. 1A and 1B. In particular, FIG. 2A illustrates a top perspective view of the receptacles 175a and 175b detached from one another. In one embodiment, the receptacle 175a has a receiver 252 that receives a connector 251 of the receptacle 175b. For example, the receiver 252 and the connector 251 may encompass one or magnets that allow for magnetic adherence between the receptacles 175a and 175b. Alternatively, other types of connection mechanisms (e.g., clips) may be used to adhere the receptacles 175a and 175b to one another. Furthermore, the receptacle 175a may have a stopper 253 that indicates an end portion of the receptacle 175a. FIG. 2B illustrates the receptacles 175a and 175b adhered to one another.

Figure 3A:
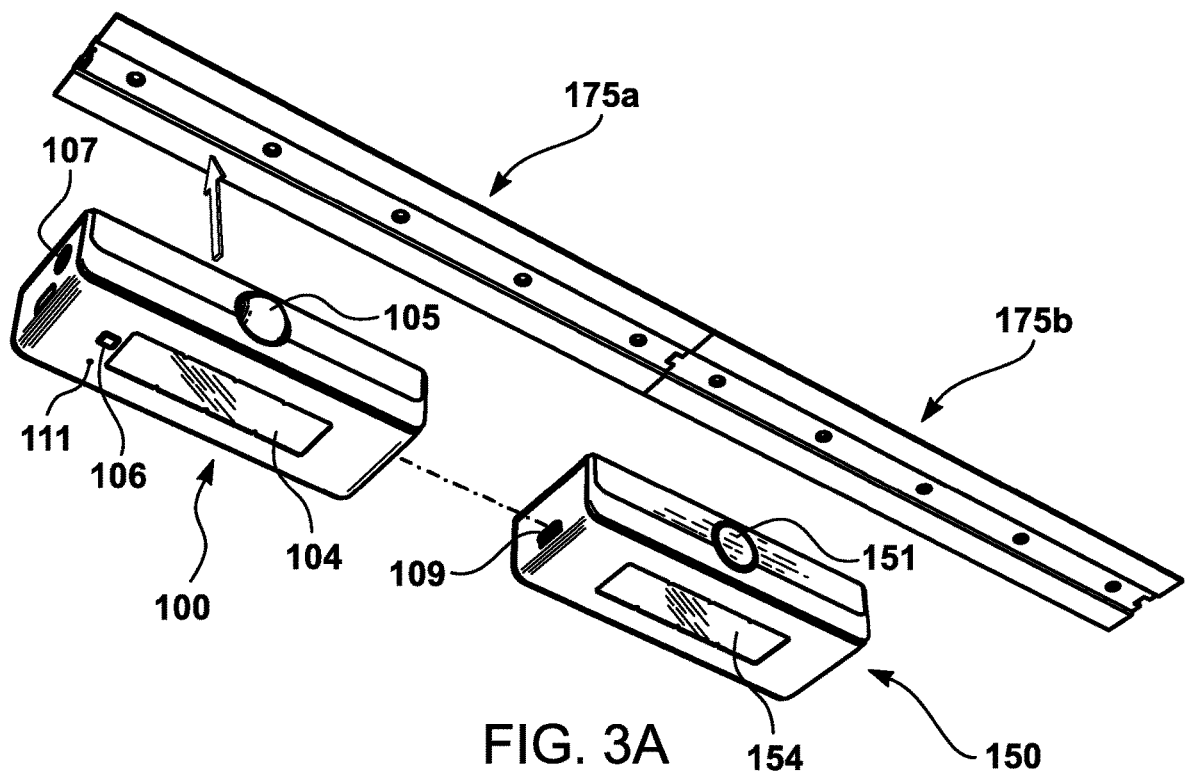
FIG. 3A illustrates an underside perspective view of the primary modular lighting unit and the extender modular lighting unit detached from one another, and detached from the receptacles.
Figure 3B:
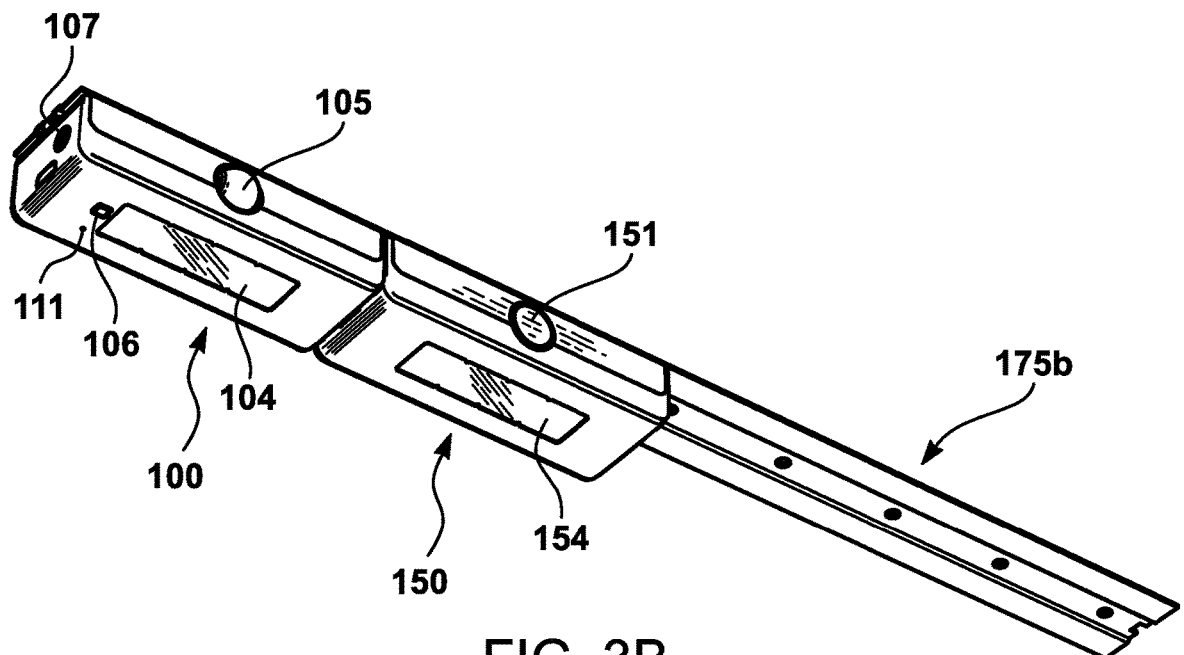
FIG. 3B illustrates an underside perspective view of the primary modular lighting unit and the extender modular lighting unit attached to one another, and attached to the receptacles.

Furthermore, FIGS. 3A and 3B illustrate underside perspective views of the receptacles 175a and 175b, in addition to underside perspective view of the primary modular lighting unit 100 and the extender modular lighting unit 150. In particular, FIG. 3A illustrates an underside perspective view of the primary modular lighting unit 100 and the extender modular lighting unit 150 detached from one another, and detached from the receptacles 175a and 175b. The primary modular lighting unit 100 has a primary light emission window 104, and the extender modular lighting unit 150 has an extender light emission window 154. In one embodiment, the primary light emission window 104 and the extender light emission window 154 have the same, or substantially similar, configurations to allow for a plurality of light emitters (e.g., LEDs) within the modular lighting units to emit light. In another embodiment, the primary light emission window 104 and the extender light emission window 154 have different configurations. FIG. 3B illustrates an underside perspective view of the primary modular lighting unit 100 and the extender modular lighting unit 150 attached to one another, and attached to the receptacles 175a and 175b.

The primary modular lighting unit 100 may also have an activator 106 that, when activated (e.g., pressed, swiped, tapped, etc.), initiates light emission from the one or more light emitters of either, or both, of the primary modular lighting unit 100 and the extender modular lighting unit 150. Furthermore, the activator 106 may also allow for changing the colors emitted by the one or more light emitters. For instance, the user may press the activator 106 with a tap to turn the light emitters on, and hold the activator 106 for a predetermined amount of time (e.g., four seconds) to enter a color configuration mode in which the color of the light emitted by the light emitters may be modified. For example, the user may be able to view the color emitted by the light emitters through the primary light emission window 104 and/or the extender light emission window 154, and cycle through the different color options via inputs to the activator 106 (e.g., taps) until the desired color is reached. In one embodiment, the user uses the activator 106 to modify all of the light emitted by the light emitters based on a single color. In an alternative embodiment, the user uses the activator 106 to modify the light emitted by the light emitters to emit different colors. Accordingly, the activator 106 positioned on the primary modular lighting unit 100 may control the lighting for the entire modular motion-detected lighting system, including the extender modular lighting unit 150, which may not have an activator 106. Furthermore, the primary modular lighting unit 100 may have a battery supply connector 107 that connects to an external A/C adaptor.

The receptacles 175a and 175b may adhered to, partially enclose, or fully enclose the primary modular lighting unit 100 and the extender modular lighting unit 150. Alternatively, the primary modular lighting unit 100 and the extender modular lighting unit 150 may be connected directly to the underside of an object (e.g., cabinet, staircase rail, shelf, etc.) without use of the receptacles 175a and 175b.

Figure 4A:
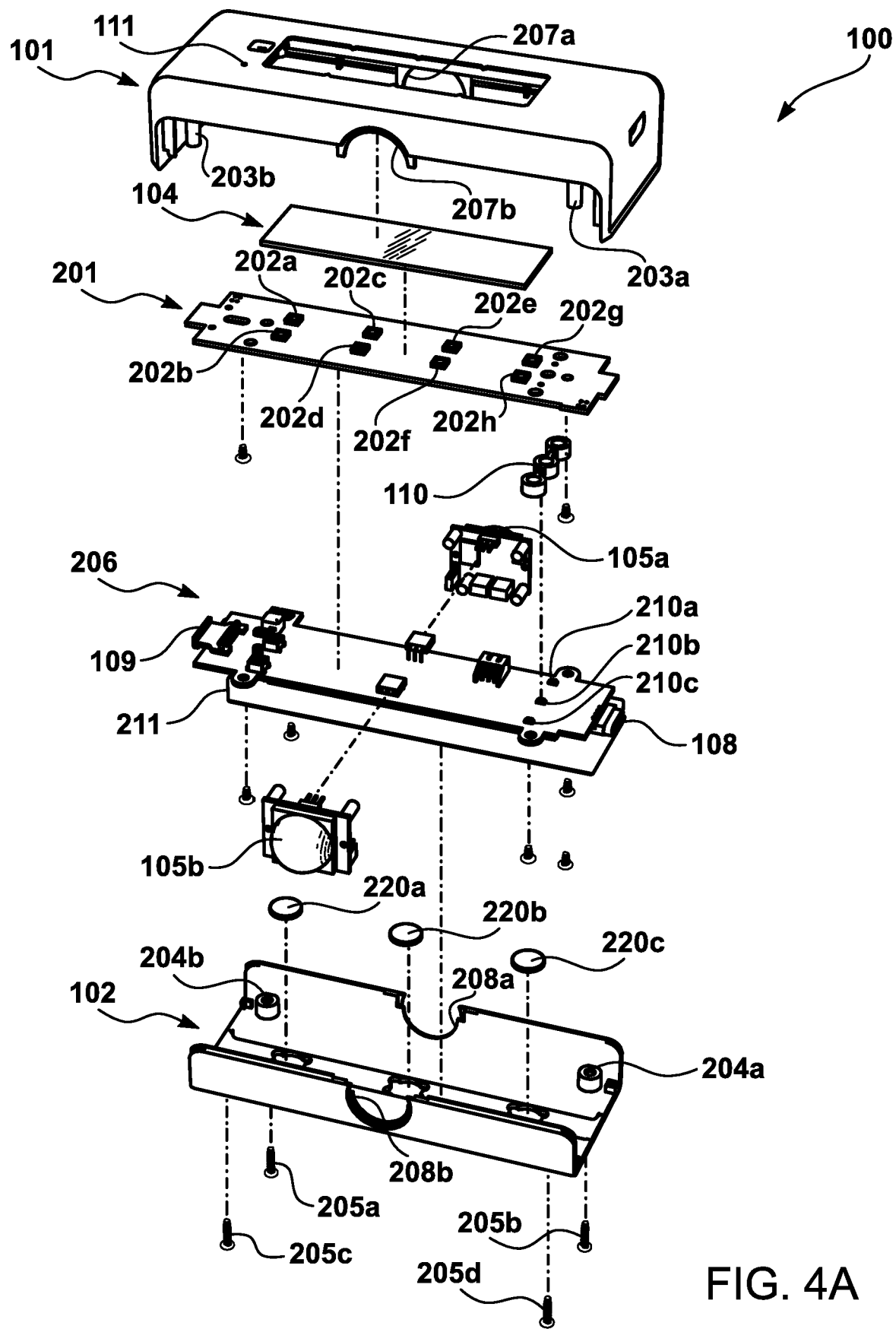
FIG. 4A illustrates a disassembled view of the primary modular lighting unit.
Figure 4B:
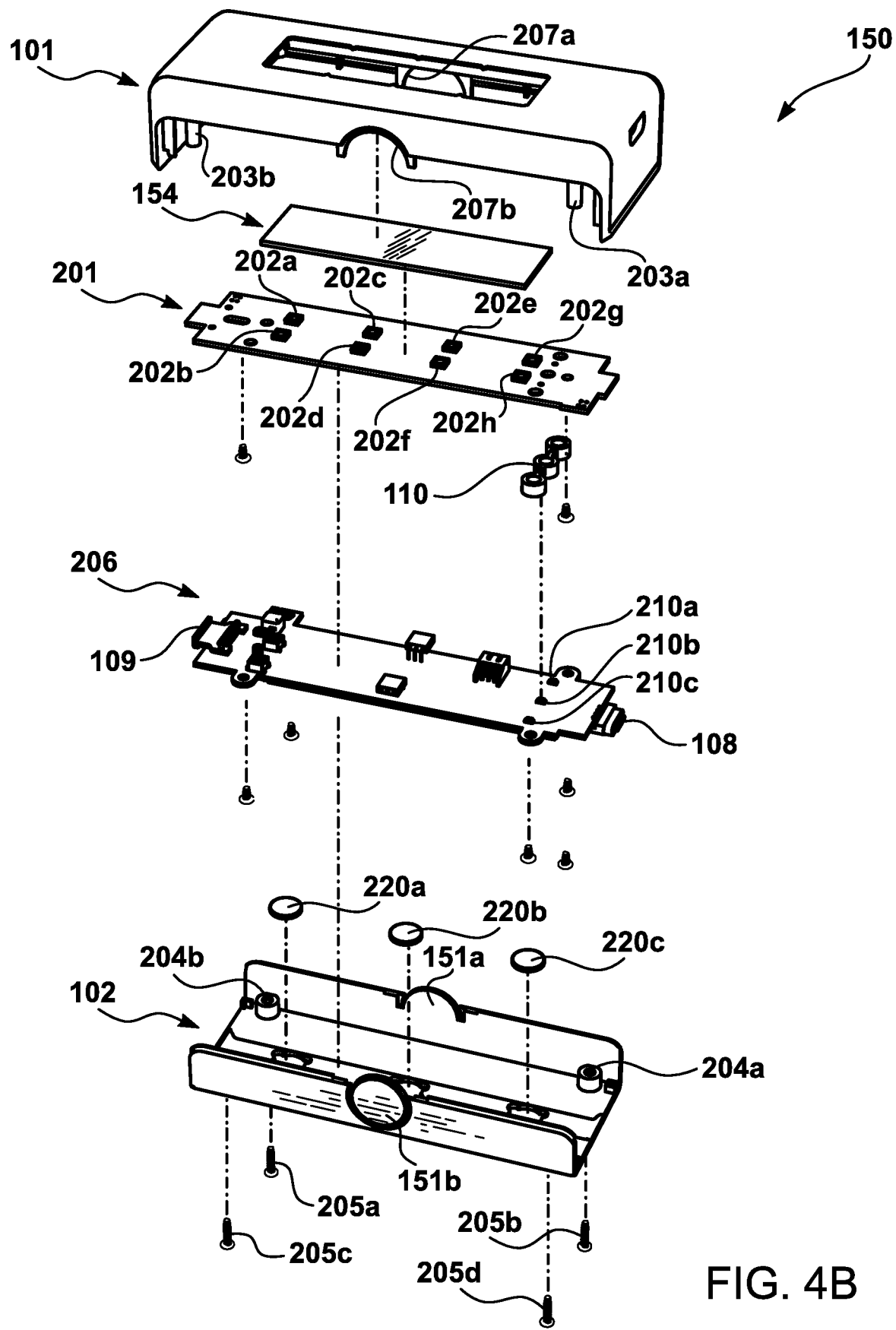
FIG. 4B illustrates a disassembled view of the extender modular lighting unit.

Furthermore, FIGS. 4A and 4B illustrate disassembled views of the primary modular lighting unit 100 and the extender modular lighting unit 150. In particular, FIG. 4A illustrates a disassembled view of the primary modular lighting unit 100. A first enclosure section 101 may have a plurality of first enclosure receivers 203a and 203b that receive one or more connectors 205a-d (e.g., screws, bolts, etc.) through one or more second enclosure receivers 204a and 204b. Furthermore, the primary modular lighting unit 100 may have a plurality printed circuit boards ("PCBs") positioned within the primary modular lighting unit 100. For example, the primary modular lighting unit 100 may have an LED board 201 on which a plurality of LEDs 202a-h are situated. The light emission window 104 may be positioned on top of the LED board 201. Furthermore, the primary modular lighting unit 100 may have a processor board 206 on which various processors may be situated for operation of the primary modular lighting unit 100 and/or extender modular lighting units 150. Additionally, the primary modular lighting unit 100 may have one or more first enclosure cavities 207a and 207b through which a portion of motion sensors 105a and 105b, as an example, may protrude, respectively. In other words, the primary modular lighting unit 100 may have multiple motion sensors. In essence, the primary modular lighting unit 100 may be a dual bi-directional forward facing motion-detected lighting apparatus that allows for motion detection within a three hundred sixty degree field of view. (Alternatively, more than two motion sensors may also be utilized.) Similarly, the primary modular lighting unit 100 may have one or more second enclosure cavities 208a and 208b through which another portion of the motion sensors 105a and 105b may protrude, respectively. Additionally, the primary modular lighting unit 100 may have positioned therein one or more magnets 220a-c for adherence to the one or more receptacles 175a and 175b illustrated in FIGS. 2A and 2B. (Other types of connectors may be utilized instead.)

Furthermore, the primary modular lighting unit 100 may have a battery supply connector 107 that charges a battery 211. As an example, the primary modular lighting unit 100 may be positioned underneath a kitchen cabinet, and be plugged into a wall outlet with an A/C adapter via the battery supply connector 107, thereby providing electricity, via electrical connectivity, throughout the modular motion-detected lighting system. Alternatively, the primary modular lighting unit 100 may be powered via an internal battery supply that is positioned within the primary modular lighting unit 100. For example, an internal rechargeable battery may be used within the primary modular lighting unit 100 to avoid having to have external wires/cables.

Optionally, the primary modular lighting unit 100 may have additional LEDs 210a-c that emit light through a light guide 110 toward the top surface of the primary modular lighting unit 100. For example, the top surface may be translucent. The additional LEDs may then emit light that is visible through the top surface from the exterior of the primary modular lighting unit 100. For instance, the additional LEDs 210a-c may be configured to emit light of a particular color(s) that is visible to a user through the top surface of the primary modular lighting unit 100.

As another option, the primary modular lighting unit 100 may have an empty cavity for the receiver 109, or connector 108, to prevent connection of modular extender lighting units from one side of the primary modular lighting unit 100. As a result, the flow of electricity may be controlled to move in one direction from the primary modular lighting unit 100 linearly through extender modular lighting units 150.

As yet another option, the primary modular lighting unit 100 may have a reset activator 111.

FIG. 4B illustrates a disassembled view of the extender modular lighting unit 150. In essence, the extender modular lighting unit 150 may have the light emitter componentry of the primary modular lighting unit 100, illustrated in FIG. 4A, without the corresponding processing and power supply componentry. Alternatively, the extender modular lighting unit 150 may have these components as well. In place of the motion sensors 105a and 105b, the extender modular lighting unit 150 may have the non-motion sensing elements 151a and 151b.

Figure 5A:
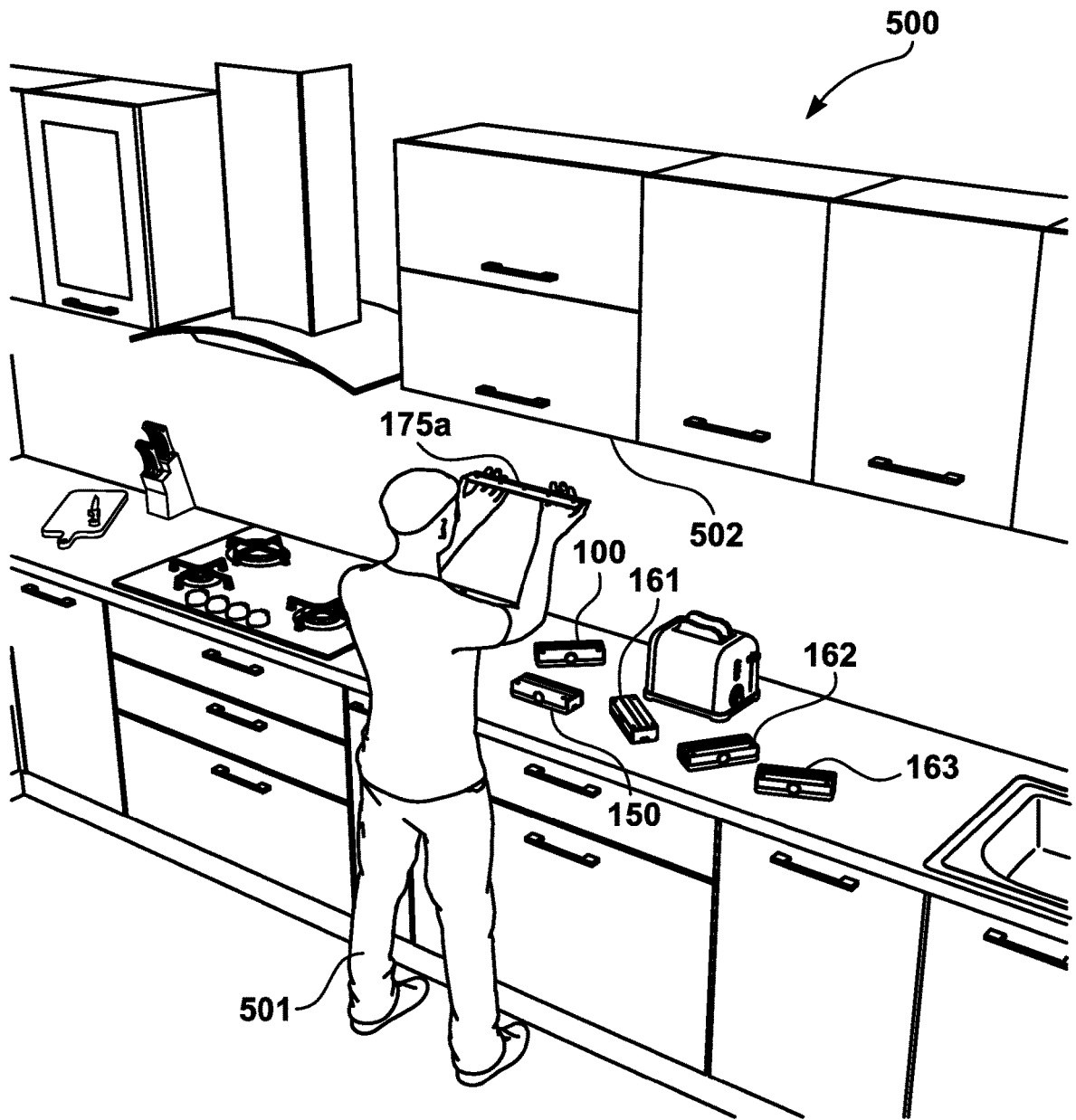
FIG. 5A illustrates the user performing a tool-less installation of the receptacles on the underside portion of the kitchen cabinet.
Figure 5B:
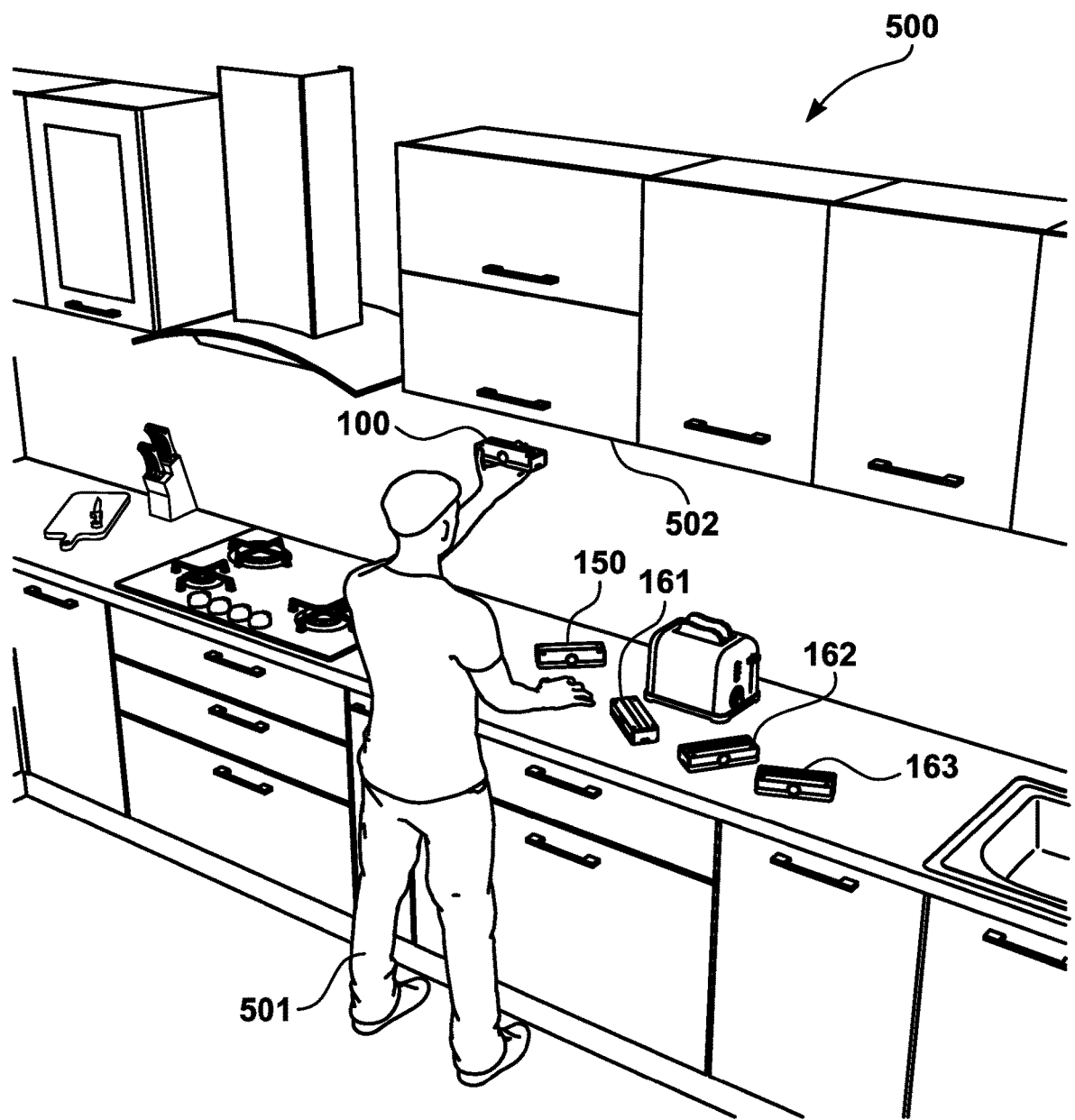
FIG. 5B illustrates the user adhering the primary modular lighting unit to the receptacle.
Figure 5C:
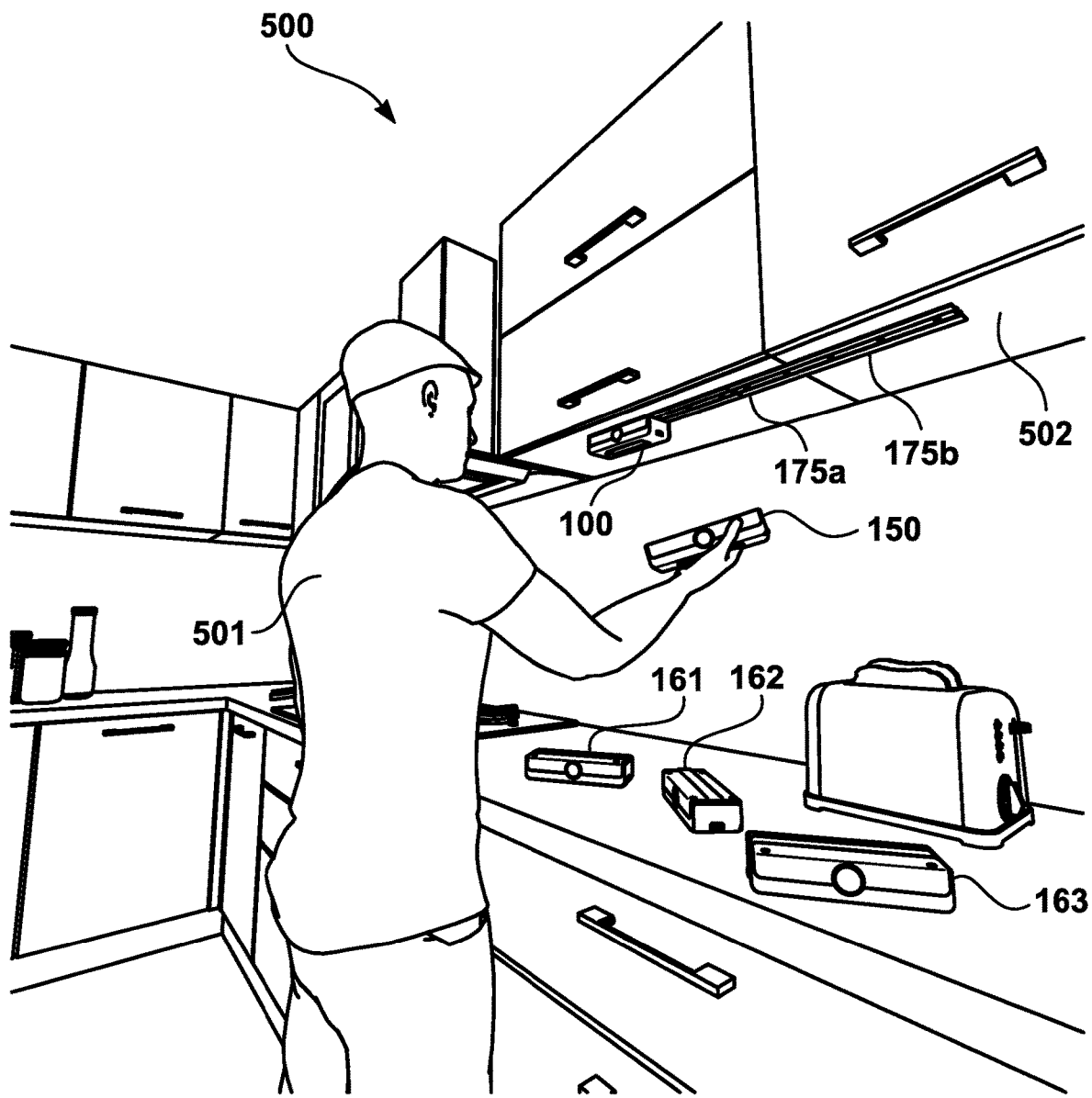
FIG. 5C illustrates the user adhering the extender modular lighting units to the receptacles.

FIGS. 5A, 5B, and 5C illustrate an example of a physical environment 500 in which a user 501 attempts to adhere the receptacles 175a and 175b to an object (e.g., the underside of a kitchen cabinet) within the physical environment 500. In particular, FIG. 5A illustrates the user 501 performing a tool-less installation of the receptacles 175a and 175b on the underside portion of the kitchen cabinet 502. Furthermore, FIG. 5B illustrates the user 501 adhering the primary modular lighting unit 100 to the receptacle 175a. Additionally, FIG. 5C illustrates the user 501 adhering the extender modular lighting units 150, 161, 162, and 163 to the receptacles 175a and 175b. Although only two receptacles 175a and 175b are illustrated, more or less than two receptacles 175a and 175b may be utilized instead. Furthermore, one primary modular lighting unit 100 and four extender modular lighting units 150, 161, 162, and 163 are illustrated as an example, but the user 501 may use a different number of extender modular lighting units in conjunction with the primary modular lighting unit 100.

Figure 6A:
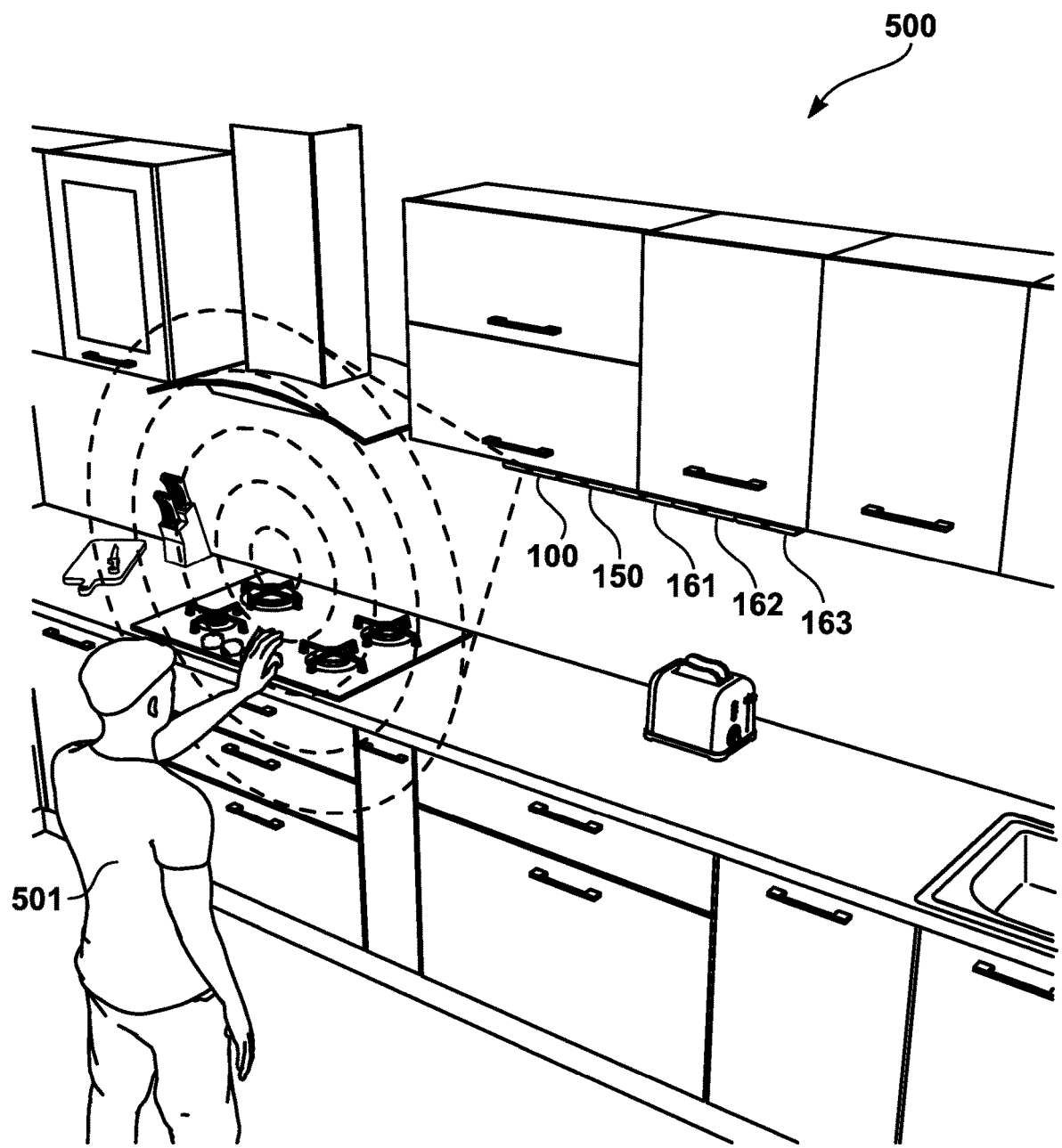
FIG. 6A illustrates the user performing a hand wave motion in front of the primary modular lighting unit.
Figure 6B:
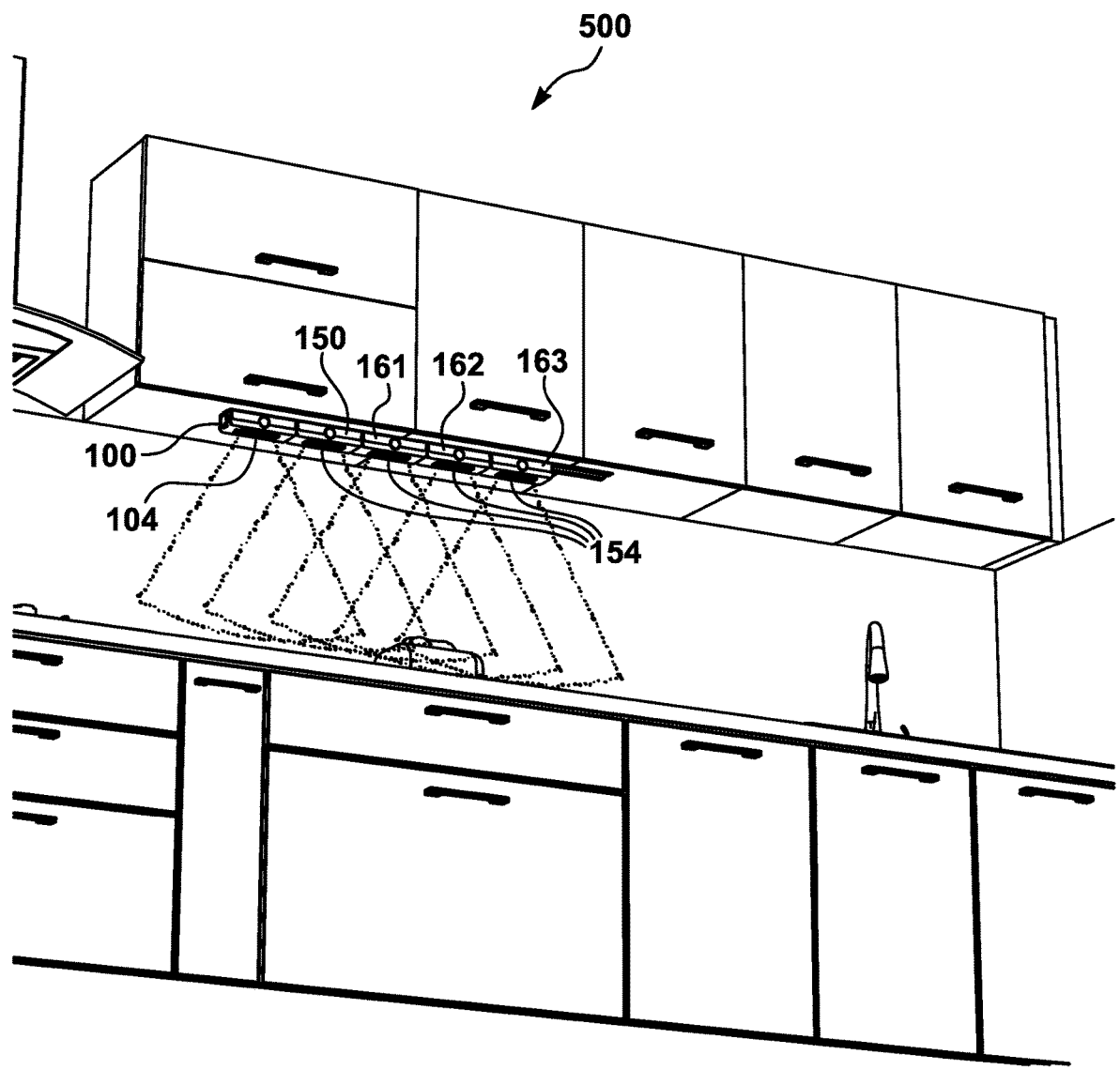
FIG. 6B illustrates the light emitted by the one or more of the plurality of LEDs through the light emission window of the primary modular lighting unit and the light emissions windows of the extender modular lighting units.

Additionally, FIGS. 6A and 6B illustrate the user 501 performing motion that activates the primary modular lighting unit 100 to instruct all of the installed modular lighting units to emit light. In particular, FIG. 6A illustrates the user 501 performing a hand wave motion in front of the primary modular lighting unit 100. The user 501 may be a considerable distance away from the primary modular lighting unit 100, and still may be detected as performing the motion. In one embodiment, any motion may activate emission of light by one or more of the plurality of LEDs 202*a*-202*h* illustrated in FIG. 3 from all of the modular lighting units 100, 150, 161, 162, and 163. In another embodiment, at least one of the motion sensors 105*a* and 105*b* may be configured to detect only movement according to a predefined pattern. For example, a horizontal hand wave may be necessary to activate light emission if the user 501 wants to avoid light emission being activated based on movement toward the primary modular lighting unit 100. Accordingly, the primary modular lighting unit 100 may be configured to recognize one or more patterns (e.g., via an image capture device that captures movements of the user 501 and a processor that performs image analysis). FIG. 6B illustrates the light emitted by the one or more of the plurality of LEDs 202*a*-202*h* through the light emission window 104 of the primary modular lighting unit 100 and the light emissions windows 154 of the extender modular lighting units 150, 161, 162, and 163.

Figure 7:
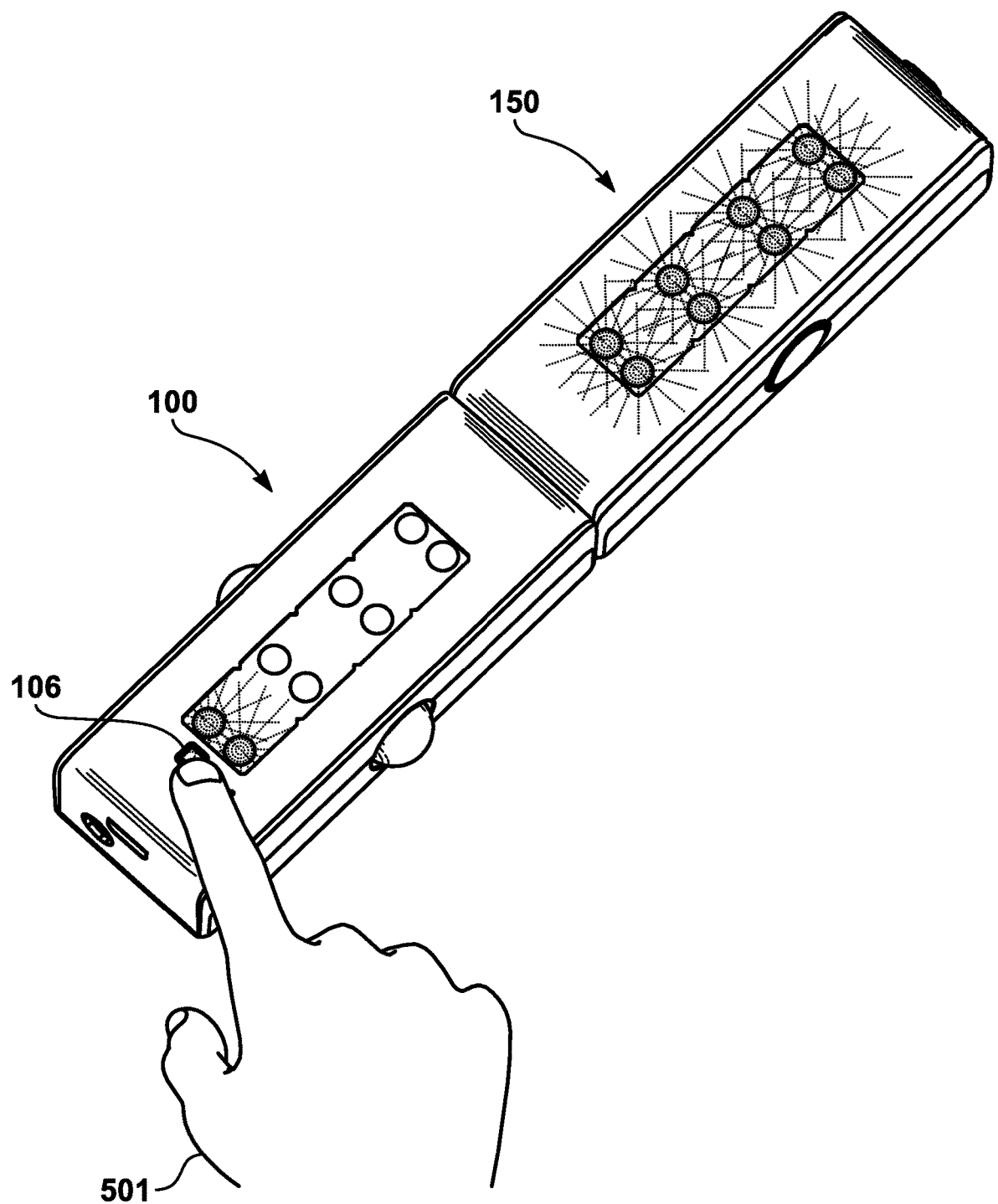
FIG. 7 illustrates the user configuring the primary modular lighting unit via an extender mode.

Additionally, FIG. 7 illustrates the user 501 configuring the primary modular lighting unit 100 via an extender mode. For example, the user 501 may activate (e.g., touch-based input) the activator 106 to enter the extender mode. In essence, the user 501 may indicate to the primary modular lighting unit 100 how many modular units are within the overall modular motion-detected lighting system via a menu. The primary modular lighting unit 100 may display, via a corresponding quantity of light emissions, the quantity of modular lighting units within the modular motion-detected lighting system. For example, the primary modular lighting unit 100 may display two light emissions from two LEDs based on the user 501 indicating that the modular motion-detected lighting system has two modular lighting units: the primary modular lighting unit 100 and the extender modular lighting unit 150.

The user 501 may also press the activator 106 to enter color configuration mode. The user 501 may view the possible colors through the light emission window 104.

Figure 8A:
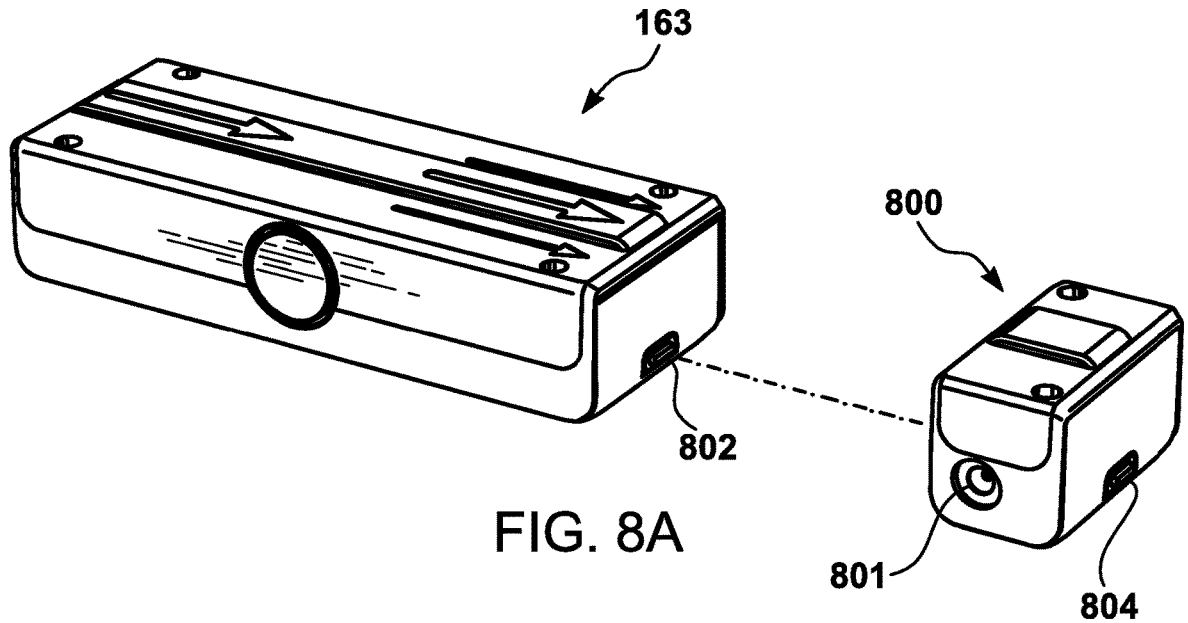
FIG. 8A illustrates a front perspective view of a power injector that may be electrically connected to an extender modular lighting unit to provide additional electrical power to the modular motion-detected lighting system to power additional extender modular lighting units.
Figure 8B:
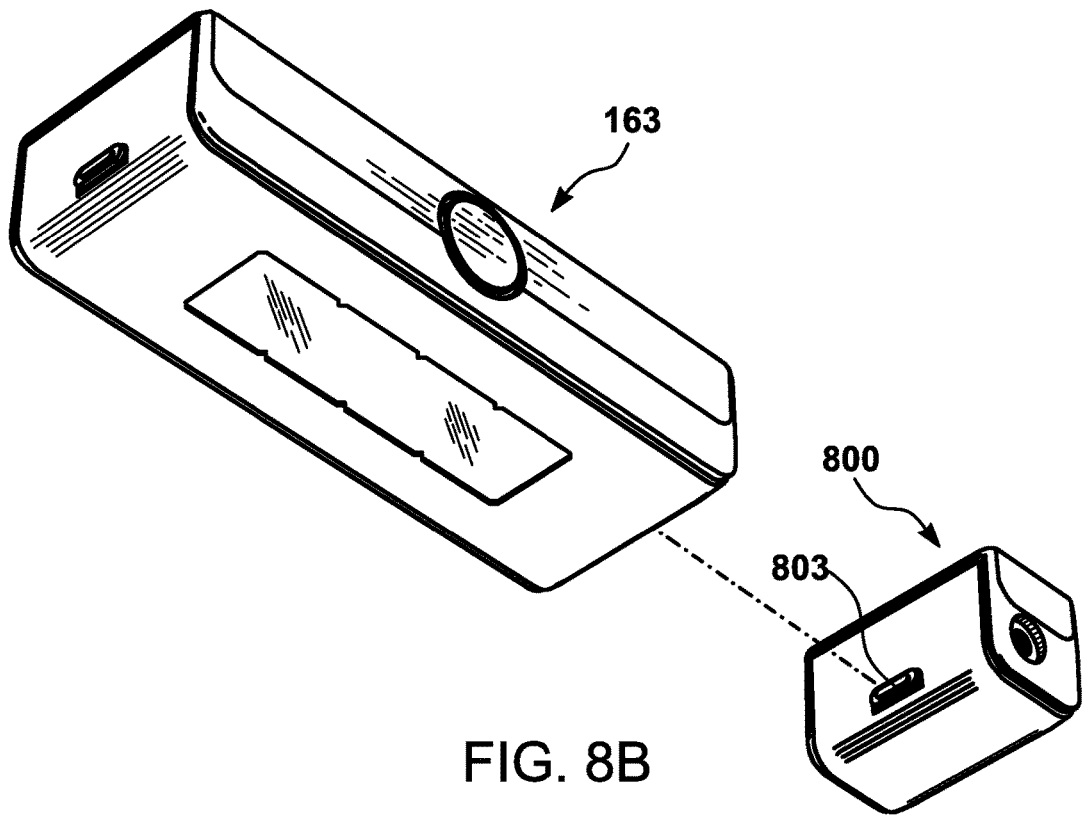
FIG. 8B illustrates an underside perspective view of the power injector and the extender modular lighting unit illustrated in FIG. 8A.

FIGS. 8A and 8B illustrate a power injection configuration to allow the modular motion-detected lighting system to receive electrical power after exceeding a predetermined quantity of modular lighting units. For example, the primary modular lighting unit 100 may be configured to provide only enough electrical power for four extender modular lighting units. FIG. 8A illustrates a front perspective view of a power injector 800 that may be electrically connected to an extender modular lighting unit 163 to provide additional electrical power to the modular motion-detected lighting system to power additional extender modular lighting units. The power injector 800 may have a battery supply connector 801 that connects to an external battery supply. Furthermore, the extender modular lighting unit 163 may have a receiver 802 for electrical connection to the power injector 801. FIG. 8B illustrates an underside perspective view of the power injector 800 and the extender modular lighting unit 163 illustrated in FIG. 8A. The power injector 800 may have a connector 803 for electrical communication with the receiver 802, illustrated in FIG. 8A, of the extender modular lighting unit 163.

Any of the electrical communication described herein may be performed with various types of receivers and/or connectors. For example, the connector 803 illustrated in FIG. 8B may be a receiver, rather than a connector.

Figure 9A:
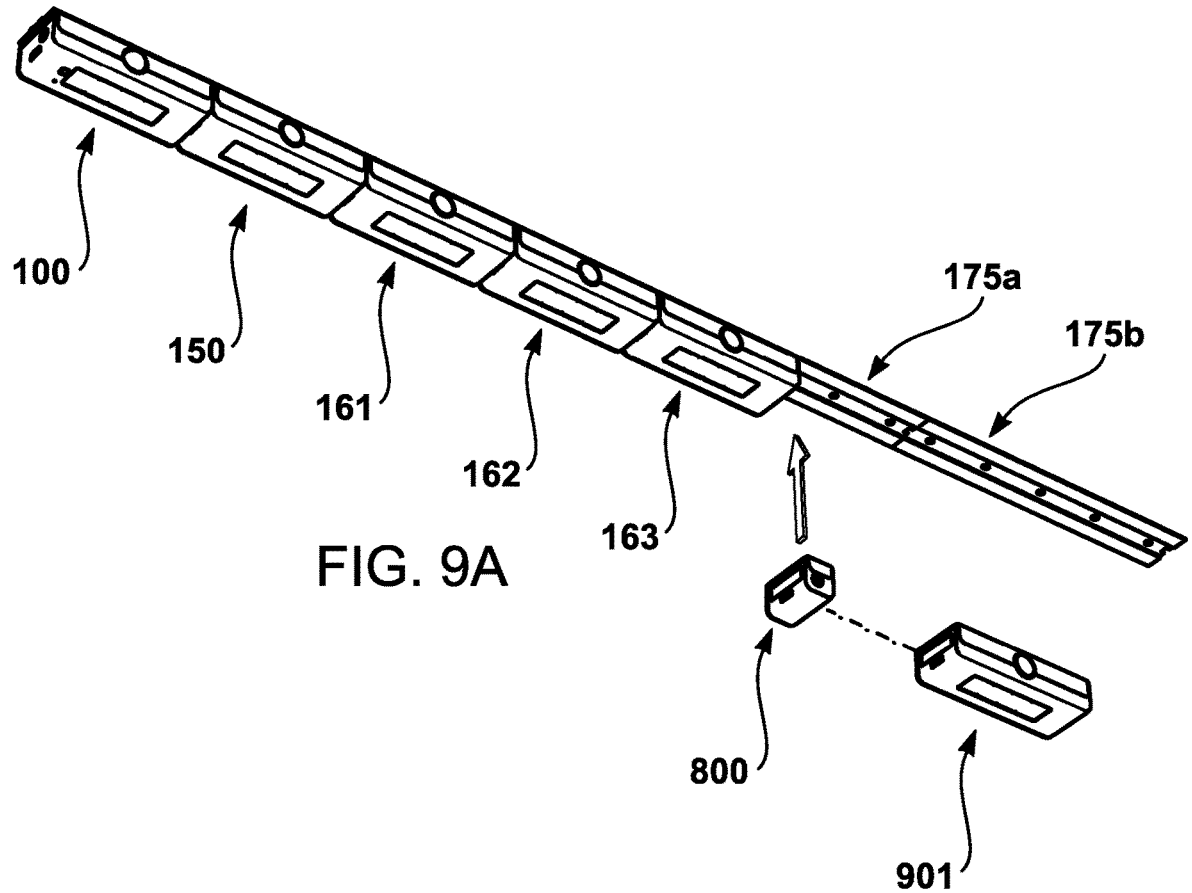
FIG. 9A illustrates the primary modular lighting unit and four extender modular lighting units positioned on one or more receptacles.
Figure 9B:
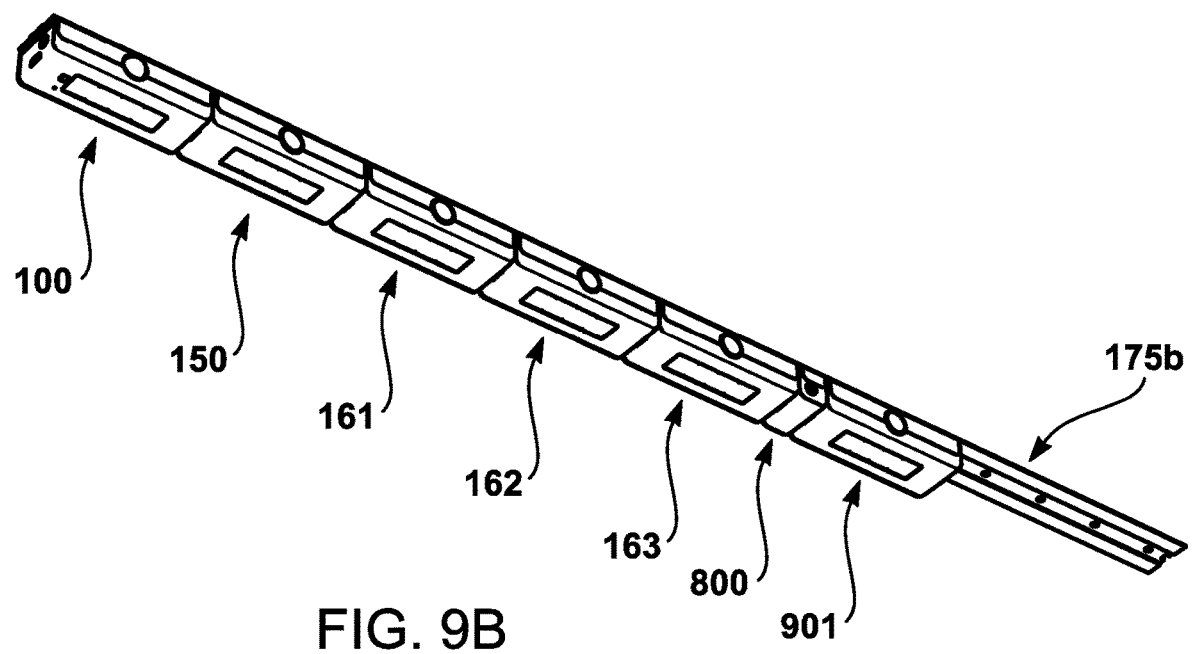
FIG. 9B illustrates the primary modular lighting unit, four extender modular lighting units, the power injector unit, and the additional extender modular lighting unit positioned on the one or more receptacles.

FIGS. 9A and 9B illustrate modular connection of multiple modular lighting units with the power injector 800 illustrated in FIGS. 8A and 8B. In particular, FIG. 9A illustrates the primary modular lighting unit 100 and four extender modular lighting units 150, 161, 162, and 163 positioned on one or more receptacles 175*a* and 175*b*. Given the predetermined threshold of five modular lighting units, the user 501 may obtain the power injector 800 to install in between the last extender modular lighting unit 163 and an additional extender modular lighting unit 901. The power injection unit 800 may also have one or more magnets, or other connectors, built-in to adhere the power injector unit 800 to the one or more receptacles 175*a* and 175*b*. FIG. 9B illustrates the primary modular lighting unit 100, four extender modular lighting units 150, 161, 162, and 163, power injector unit 800, and additional extender modular lighting unit 901 positioned on one or more receptacles 175*a* and 175*b*.

In another embodiment, a germicidal motion-detected lighting system may be implemented utilizing the primary modular lighting unit 100 and at least one extender modular lighting unit 150. In essence, the germicidal motion-detected lighting system may be positioned within a home to emit visible light when motion of a user is detected, and switch to emitting ultraviolet light only when motion of the user is not detected, such as when the user is not in close proximity to the germicidal motion-detected lighting system. Accordingly, the germicidal motion-detected lighting system automatically provides visible light in the presence of a user, and automatically switches to optical disinfection when the user is safely away from it.

In particular, the optical disinfection encompasses emitting ultraviolet light (i.e., light ranging from one hundred nanometers to four hundred nanometers) toward a surface (e.g., kitchen countertop) to eliminate the germs and biofilms resting on that surface. For instance, the ultraviolet light may generate oxide radicals that penetrate below the surface at which the ultraviolet light is emitted. In one embodiment, the unit responsible for emitting the ultraviolet light (i.e., the primary modular lighting unit 100 or the extender modular lighting unit 150) may emit the ultraviolet light in a pulsation pattern to perform the optical disinfection. A variety of duty cycles (e.g., within an approximate range of thirty percent to seventy percent) may be utilized for the pulsation; however, a duty cycle of approximately fifty percent (i.e., one pulse for every two units of time) may provide optimal disinfection. (The range of thirty percent to seventy percent is provided only as an example; other ranges (e.g., twenty percent to eighty percent, or even zero percent to one hundred percent) may be utilized instead.) Furthermore, an example of the pulsation frequency may be in the range of zero to one thousand hertz.

In one embodiment, the ultraviolet light is specifically restricted to Ultraviolet A (i.e., a wavelength of three hundred fifteen nanometers to four hundred nanometers) to provide for reliable optical disinfection, while also being relatively benign to humans and animals. In other embodiments, although more harmful than Ultraviolet A, ultraviolet light of longer wavelengths (e.g., Ultraviolet B (a wavelength in the range of two hundred eighty nanometers to three hundred fifteen nanometers) and Ultraviolet C (a wavelength in the range of one hundred nanometers to two hundred eighty nanometers)) may be utilized, given the automatic deactivation of ultraviolet light emission based on motion detected by a processor in the primary modular lighting unit 100. (Alternatively, the processor may be positioned within the extender modular lighting unit 150.)

The germicidal motion-detected lighting system may have one activation mechanism (e.g., button) that activates, or motion deactivates, an optical disinfection module. As an example, after activation of a button, a built-in timer may be configured to tally a predetermined time period before emitting the optical light emission, thereby allowing a user to move out of proximity of the optical disinfection. Furthermore, the germicidal motion-detected lighting system may have one or more optical disinfection modules. As a result, the germicidal motion-detected lighting system provides for a modular solution that is scalable for use with a variety of different sized-environments (e.g., kitchen countertops of varying lengths). As an alternative, the germicidal motion-detected lighting system may have one or more visible light emission modules that are activated upon motion, and one or more optical disinfection modules that are deactivated upon the motion. In this configuration, digital inter-module communication allows for communication of motion detected from one module to be relayed in the form of the motion signal, or a resulting activation/deactivation command, to another module, thereby obviating the necessity of having multiple motion sensors, each on a respective module; in other words one module may have the one or more motion sensors, while the other modules do not have to have motion sensors. However, in an alternative configuration, each module (visible light emission or optical disinfection) may have its own motion sensor. Furthermore, the modules may be controlled via a wireless configuration.

Figure 10A:
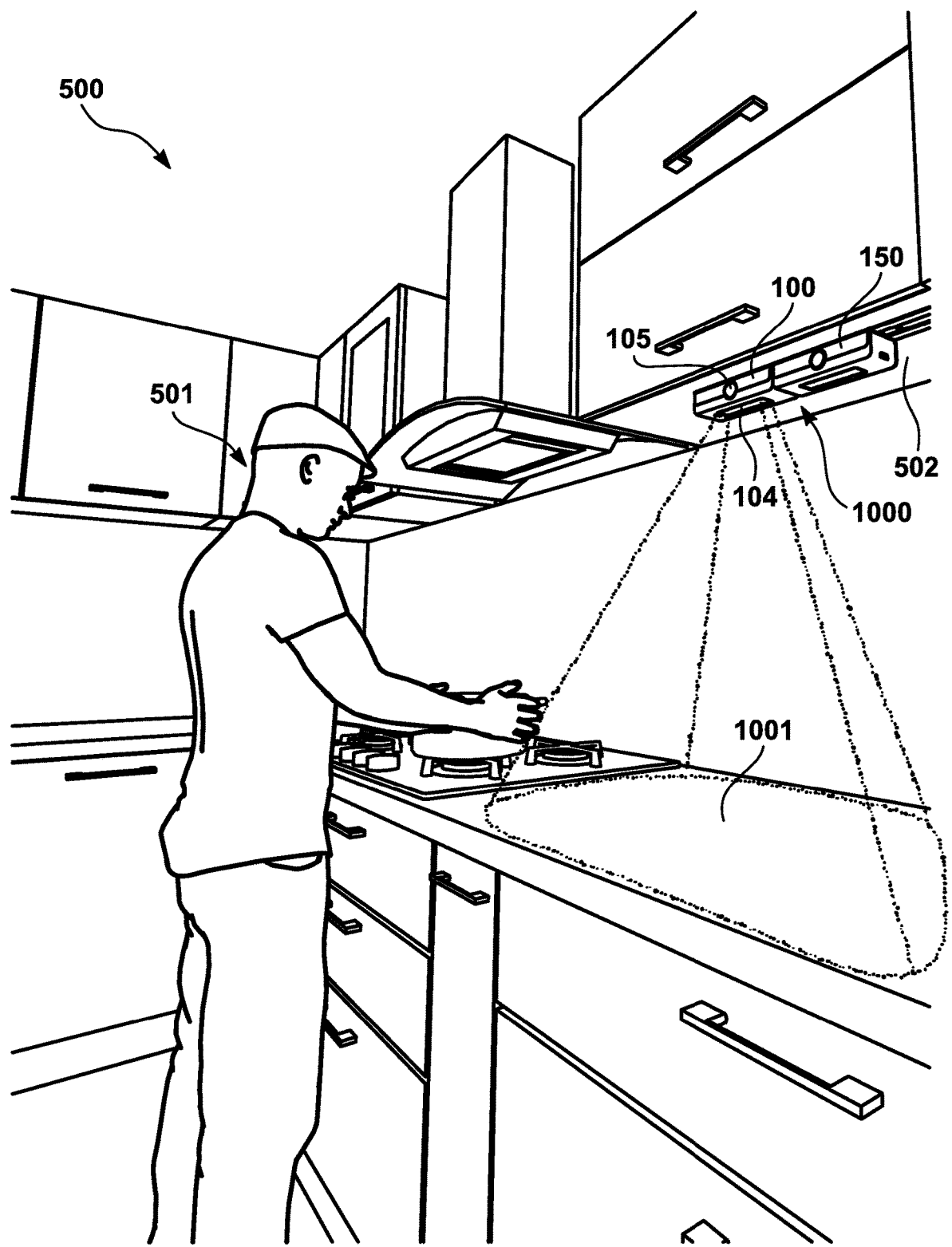
FIG. 10A illustrates the germicidal motion-detected lighting system being adhered to the underside of a kitchen cabinet, and emitting visible light.
Figure 10B:
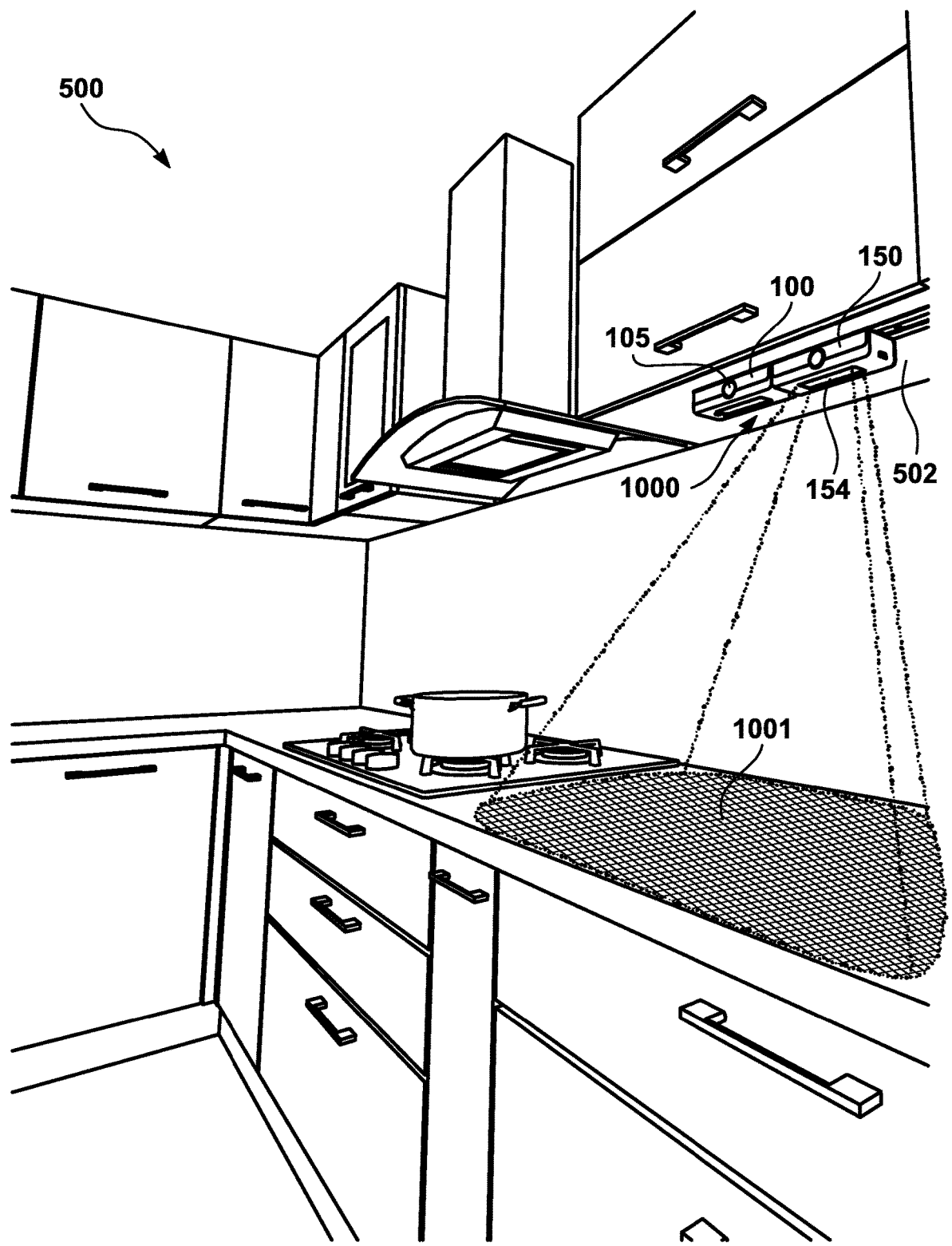
FIG. 10B illustrates the germicidal motion-detected lighting system, illustrated in FIG. 10A, emitting ultraviolet light instead of visible light.

FIGS. 10A and 10B illustrate an example of a germicidal motion-detected lighting system 1000. In particular, FIG. 10A illustrates the germicidal motion-detected lighting system 1000 being adhered to the underside of the kitchen cabinet 502. Given that the user 501 is present within the kitchen 500, the motion sensor 105 of the primary modular lighting unit 100 detects the motion of the user 501. Based upon such detection, the processor within the primary modular lighting unit 100 ensures that only LEDs that are specifically configured to emit visible light perform such light emission. In other words, in the presence of the user 501, the processor ensures that safe visible light is emitted, rather than ultraviolet light for optical disinfection. In one embodiment, as illustrated in FIG. 10A, the primary modular lighting unit 100 may be responsible for emitting visible light, whereas the extender modular lighting unit 150 may be responsible for emitting ultraviolet light. Accordingly, the primary modular lighting unit 100 may have LEDs specifically configured to emit visible light, whereas the extender modular lighting unit 150 may have LEDs specifically configured to emit ultraviolet light. Upon detection of the motion of the user 501, the processor activates visible light emission from the primary modular lighting unit 100, while deactivating ultraviolet light emission from the extender modular lighting unit 150.

By way of contrast, FIG. 10B illustrates a switch to ultraviolet light emission. Upon detecting a lack of motion by the user 501, or another user or animal, the motion sensor 105 communicates such lack of motion to the processor. As a result, the processor, which is positioned within the primary modular lighting unit 100 that is in operable communication with the extender modular lighting unit 150, deactivates visible light emission from the primary modular lighting unit 100, and activates ultraviolet light emission from the extender modular lighting unit 150. The ultraviolet light emission may be directed toward a surface, such as a kitchen countertop 1001, to eradicate germs and biofilms resting on the kitchen countertop 1001. In one embodiment, the ultraviolet emission is performed in a pulsation pattern. In another embodiment, the ultraviolet emission is performed in a continuous manner without pulsations.

Although FIGS. 10A and 10B illustrate the primary modular lighting unit 100 being responsible for visible light emission and the extender modular lighting unit 150 being responsible for ultraviolet light emission, in another embodiment, the roles are reversed. In yet another embodiment, one or more modular units may each have the capability of switching between visible light emission and ultraviolet light emission from the same unit. For example, one modular unit may have both visible light LEDs and ultraviolet light LEDs, allowing the processor within the modular unit to seamlessly switch between visible light emission and ultraviolet light emission. Furthermore, in another embodiment, without visible light emission, one or more modular units may be activated to emit ultraviolet light upon motion detection, and deactivated to cease emitting ultraviolet light upon a lack of motion detection. For example, the user 501 may want to optically disinfect a surface in a room with windows during daylight hours when the user 501 is not present within that room, but may not want visible light to be emitted upon entry of the user 501 into the room during those daylight hours.

Figure 11:
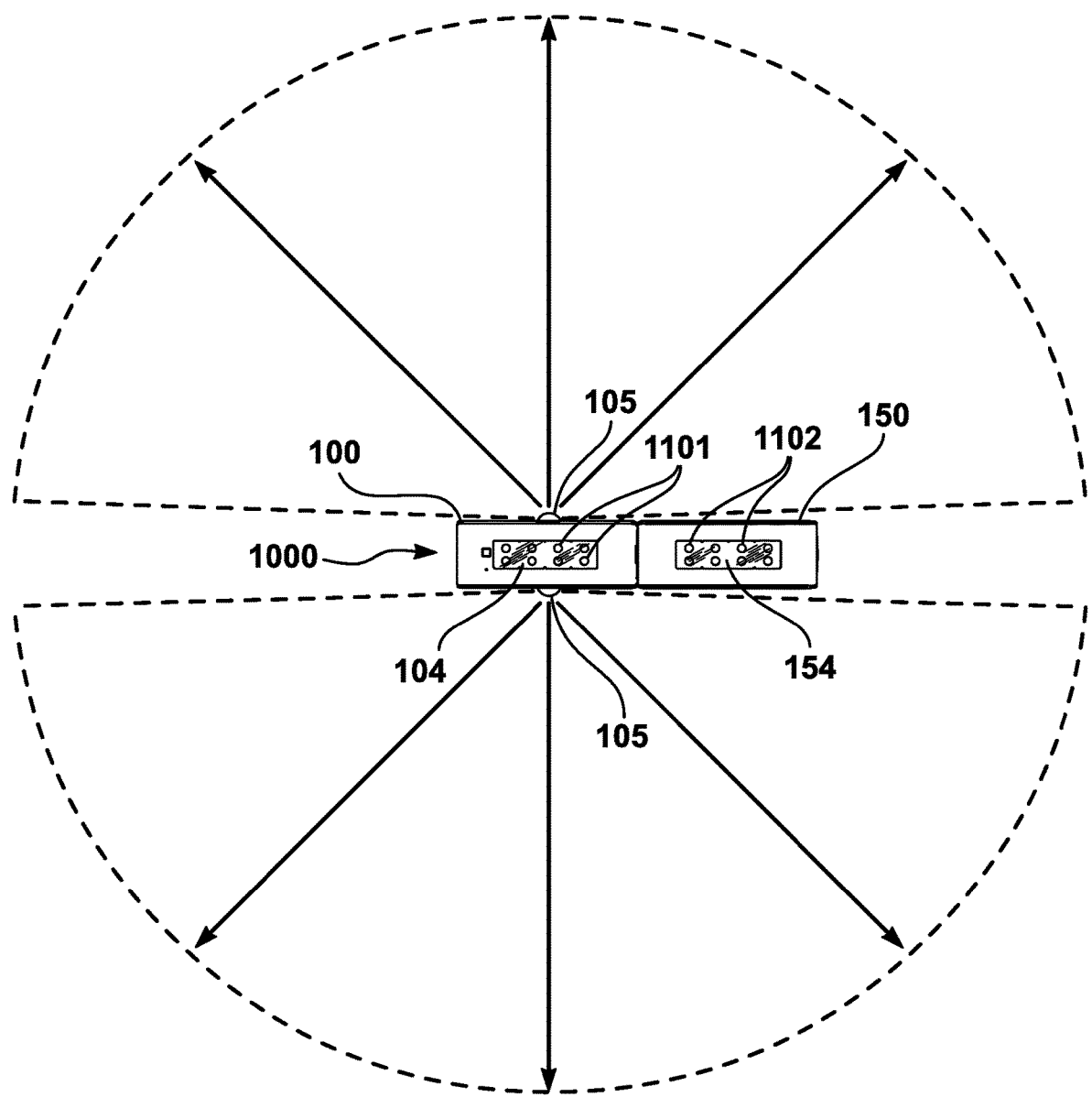
FIG. 11 illustrates a top view of the germicidal motion-detected lighting system, and the range at which motion is detected around the germicidal motion-detected lighting system.

FIG. 11 illustrates a top view of the germicidal motion-detected lighting system 1000, and the range at which motion is detected around the germicidal motion-detected lighting system 1000. In particular, the range may be substantially three hundred sixty-five degrees, which may result in a diameter of approximately sixty feet. (The term "substantially" is intended to refer to a value within a tolerance threshold of approximately twenty to thirty percent of the indicated value.) Accordingly, the germicidal motion-detected lighting system 1000 is able to detect motion within a significant distance, thereby deactivating ultraviolet illumination well in advance of human, or animal, proximity, thereby enhancing the safety of optical disinfection. (The distance of sixty feet is provided only as an example of how the germicidal motion-detected lighting system 1000 can provide optical disinfection at a distance. Accordingly, other distances may be applicable. For example, a given physical environment may have various barriers (e.g., walls) that potentially shorten the distance for motion detection.)

Furthermore, the top view of the germicidal motion-detected lighting system 1000 illustrates a plurality of visible light LEDs 1101, positioned within the primary modular lighting unit 100, and a plurality of ultraviolet light LEDs 1102, positioned within the extender modular lighting unit 150. Although only one primary modular lighting unit 100 and one extender modular lighting unit 150 are illustrated, additional primary modular lighting units 100 and one extender modular lighting units 150 may be utilized to provide additional visible light and/or additional optical disinfection.

It is understood that the apparatuses and systems described herein may also be applied in other types of apparatuses and systems. Those skilled in the art will appreciate that the various adaptations and modifications of the embodiments of the apparatuses described herein may be configured without departing from the scope and spirit of the present apparatuses. Therefore, it is to be understood that, within the scope of the appended claims, the present apparatuses may be practiced other than as specifically described herein.

We claim:
1. A germicidal motion-detecting lighting system comprising:
  a primary modular lighting unit having a first enclosure with first and second cavities, a first light emission window positioned within the first cavity, a first plu- rality of light emitting diodes positioned within the first enclosure, at least one motion sensor protruding through the second cavity, one or more geometrically-shaped casings that surround the at least one motion sensor, and a processor positioned within the first enclosure that detects motion of a user based on data received from the at least one motion sensor and generates an activation command to emit visible light based on the motion of the user, the first plurality of light emitting diodes receiving the activation command and emitting the visible light based on the activation command; and a first extender modular lighting unit having a second enclosure with a third cavity, a second light emission window positioned within the third cavity, a second plurality of light emitting diodes that are positioned within the second enclosure, and one or more non-motion sensing elements in a position that corresponds to the one or more geometrically-shaped casings of the primary modular lighting unit, the second plurality of light emitting diodes emitting ultraviolet light prior to the processor detecting the motion of the user, the second plurality of light emitting diodes ceasing to emit the ultraviolet light upon the processor detecting the motion of the user based on a deactivation command received from the processor.

2. The germicidal motion-detecting lighting system of claim 1, wherein the at least one motion sensor determines the motion of the user via a range substantially spanning three hundred sixty-five degrees around the primary modular lighting unit.

3. The germicidal motion-detecting lighting system of claim 1, wherein the at least one motion sensor comprises an infrared sensor.

4. The germicidal motion-detecting lighting system of claim 1, wherein the visible light has a wavelength in the range of four hundred nanometers to seven hundred nanometers.

5. The germicidal motion-detecting lighting system of claim 1, wherein the ultraviolet light is Ultraviolet A light that has a wavelength in the range of three hundred fifteen nanometers to four hundred nanometers.

6. The germicidal motion-detecting lighting system of claim 1, wherein the ultraviolet light is Ultraviolet B light that has a wavelength in the range of two hundred eighty nanometers to three hundred fifteen nanometers.

7. The germicidal motion-detecting lighting system of claim 1, wherein the ultraviolet light is Ultraviolet C light that has a wavelength in the range of one hundred nanometers to two hundred eighty nanometers.

8. The germicidal motion-detecting lighting system of claim 1, germicidal motion-detected lighting system of claim 1, wherein the ultraviolet light has a wavelength in the range of one hundred nanometers to four hundred nanometers.

9. The germicidal motion-detecting lighting system of claim 1, wherein the second plurality of light emitting diodes emit the ultraviolet light according to a pulsation pattern.

10. The germicidal motion-detecting lighting system of claim 9, wherein the pulsation pattern operates at a duty cycle in a range of thirty percent to seventy percent.

11. A germicidal motion-detecting lighting system comprising:

a primary modular lighting unit having a first enclosure with first and second cavities, a first light emission window that is positioned within the first cavity, a first plurality of light emitting diodes positioned within the first enclosure, at least one motion sensor that protrudes through the second cavity, one or more geometrically-shaped casings that surround the at least one motion sensor, and a processor positioned within the first enclosure that detects motion of a user based on data received from the at least one motion sensor and generates an activation command to emit ultraviolet light based on motion inactivity of the user, the first plurality of light emitting diodes receiving the activation command and emitting the ultraviolet light based on the activation command, the first plurality of light emitting diodes ceasing to emit the ultraviolet light upon the processor detecting motion of the user based on a deactivation command received from the processor; and a first extender modular lighting unit having a second enclosure with a third cavity, a second light emission window positioned within the third cavity, a second plurality of light emitting diodes positioned within the second enclosure, and one or more non-motion sensing elements in a position that corresponds to the one or more geometrically-shaped casings of the primary modular lighting unit, the second plurality of light emitting diodes emitting visible light subsequent to the processor detecting the motion of the user.

12. The germicidal motion-detecting lighting system of claim 11, wherein the at least one motion sensor determines the motion of the user via a range substantially spanning three hundred sixty-five degrees around the primary modular lighting unit.

13. The germicidal motion-detecting lighting system of claim 11, wherein the at least one motion sensor comprises an infrared sensor.

14. The germicidal motion-detecting lighting system of claim 11, wherein the visible light has a wavelength in the range of four hundred nanometers to seven hundred nanometers.

15. The germicidal motion-detecting lighting system of claim 11, wherein the ultraviolet light is Ultraviolet A light that has a wavelength in the range of three hundred fifteen nanometers to four hundred nanometers.

16. The germicidal motion-detecting lighting system of claim 11, wherein the ultraviolet light is Ultraviolet B light that has a wavelength in the range of two hundred eighty nanometers to three hundred fifteen nanometers.

17. The germicidal motion-detecting lighting system of claim 11, wherein the ultraviolet light is Ultraviolet C light that has a wavelength in the range of one hundred nanometers to two hundred eighty nanometers.

18. The germicidal motion-detecting lighting system of claim 11, germicidal motion-detected lighting system of claim 11, wherein the ultraviolet light has a wavelength in the range of one hundred nanometers to four hundred nanometers.

19. The germicidal motion-detecting lighting system of claim 11, wherein the first plurality of light emitting diodes emit the ultraviolet light according to a pulsation pattern.

20. The germicidal motion-detecting lighting system of claim 19, wherein the pulsation pattern operates at a duty cycle in a range of thirty percent to seventy percent.

* * * * *